United States Patent
Ly et al.

(10) Patent No.: US 11,406,285 B2
(45) Date of Patent: Aug. 9, 2022

(54) EXOSUIT SYSTEMS AND METHODS FOR POSTURE SESSION SEGMENTATION AND BIOMECHANICAL FEEDBACK

(71) Applicant: SEISMIC HOLDINGS, INC., Menlo Park, CA (US)

(72) Inventors: Daniel Le Ly, Mountain View, CA (US); Andrew Robert Chang, Sunnyvale, CA (US); Chung-Che Charles Wang, Palo Alto, CA (US)

(73) Assignee: Seismic Holdings, Inc., Menlo Park, CA (US)

( * ) Notice: Subject to any disclaimer, the term of this patent is extended or adjusted under 35 U.S.C. 154(b) by 398 days.

(21) Appl. No.: 16/406,597

(22) Filed: May 8, 2019

(65) Prior Publication Data

US 2020/0000377 A1 Jan. 2, 2020

Related U.S. Application Data

(60) Provisional application No. 62/668,262, filed on May 8, 2018.

(51) Int. Cl.
| | |
|---|---|
| G08B 23/00 | (2006.01) |
| A61B 5/11 | (2006.01) |
| G08B 21/04 | (2006.01) |
| A61B 5/00 | (2006.01) |
| A61H 3/00 | (2006.01) |
| G06K 9/62 | (2022.01) |

(52) U.S. Cl.
CPC .......... *A61B 5/1116* (2013.01); *A61B 5/4561* (2013.01); *A61B 5/486* (2013.01); *A61B 5/6804* (2013.01); *A61B 5/7455* (2013.01); *A61H 3/00* (2013.01); *G06K 9/6218* (2013.01); *G06K 9/6267* (2013.01); *G08B 21/0446* (2013.01); *A61H 2201/0169* (2013.01); *A61H 2201/165* (2013.01); *A61H 2230/625* (2013.01)

(58) Field of Classification Search
CPC ..... A61B 5/1116; A61B 5/6804; A61B 5/486; A61B 5/7455; A61B 5/4561; A61B 5/0022; A61H 3/00; A61H 2230/625; A61H 2201/165; A61H 2201/0169; G06K 9/6218; G06K 9/6267; G08B 21/0446; G16H 40/67
See application file for complete search history.

(56) References Cited

U.S. PATENT DOCUMENTS

| | | |
|---|---|---|
| 8,928,484 B2 | 1/2015 | Chang et al. |
| 9,266,233 B2 | 2/2016 | Kornbluh et al. |
| 9,936,900 B2 | 4/2018 | Chang et al. |
| 9,940,811 B2 | 4/2018 | Chang et al. |
| 2013/0015976 A1* | 1/2013 | Chang .................. A61B 5/4561 340/573.7 |

(Continued)

FOREIGN PATENT DOCUMENTS

WO 2016/138264 A1 9/2016

*Primary Examiner* — Dhaval V Patel
(74) *Attorney, Agent, or Firm* — Van Court & Aldridge LLP

(57) ABSTRACT

Systems and methods for monitoring posture of a user wearing an exosuit are discussed herein. Exosuits worn by users can monitor several movement factors that characterize the user's movements and posture. The user's posture is identified and analyzed, and feedback is provided to the user based on the analyzed posture.

20 Claims, 18 Drawing Sheets

(56) References Cited

U.S. PATENT DOCUMENTS

2017/0258374 A1* 9/2017 Ly .................... A61B 5/486
2018/0056104 A1* 3/2018 Cromie ............ A63B 21/4039
2018/0264320 A1* 9/2018 Chang ................ A61B 5/1122

* cited by examiner

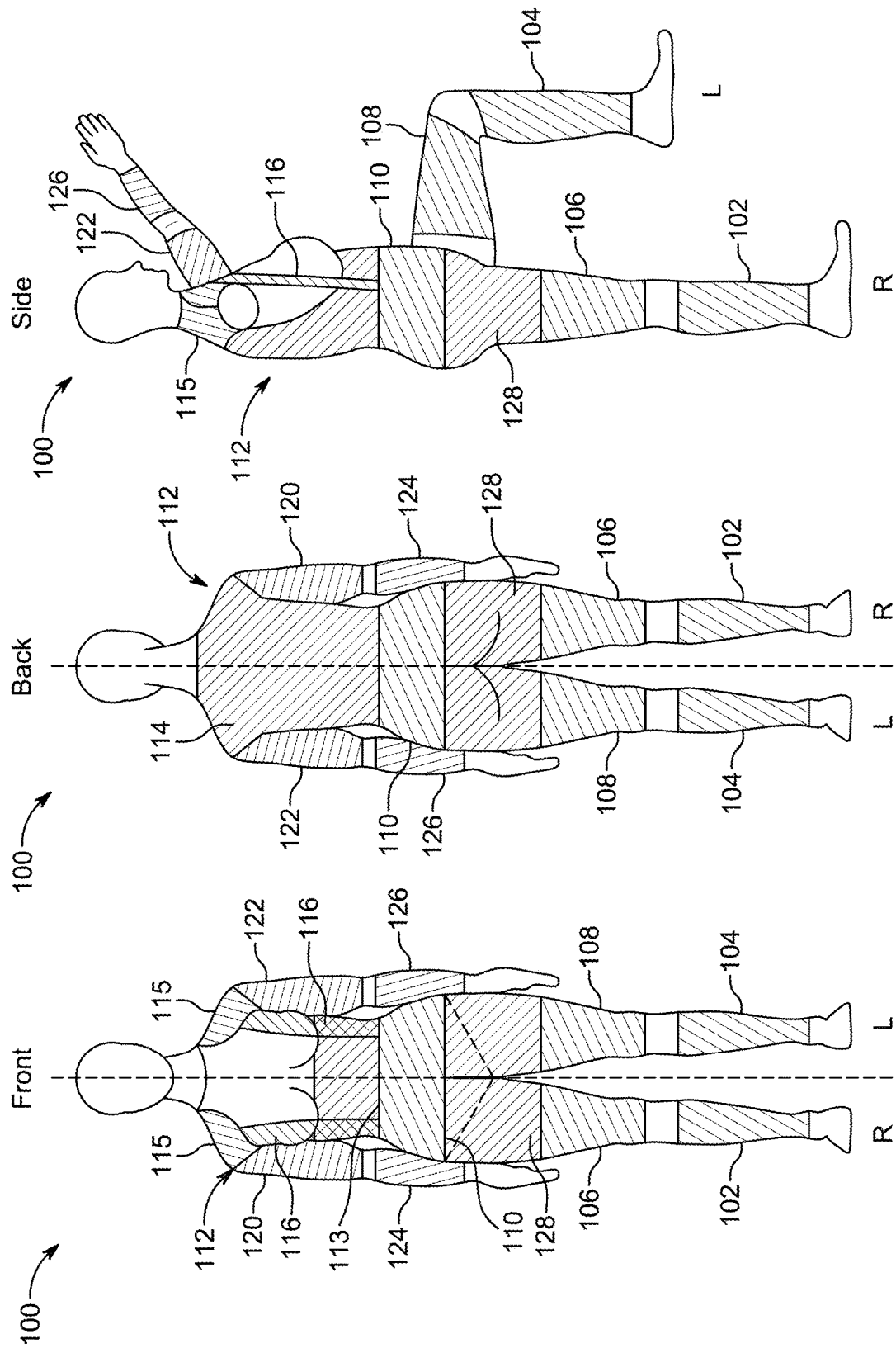

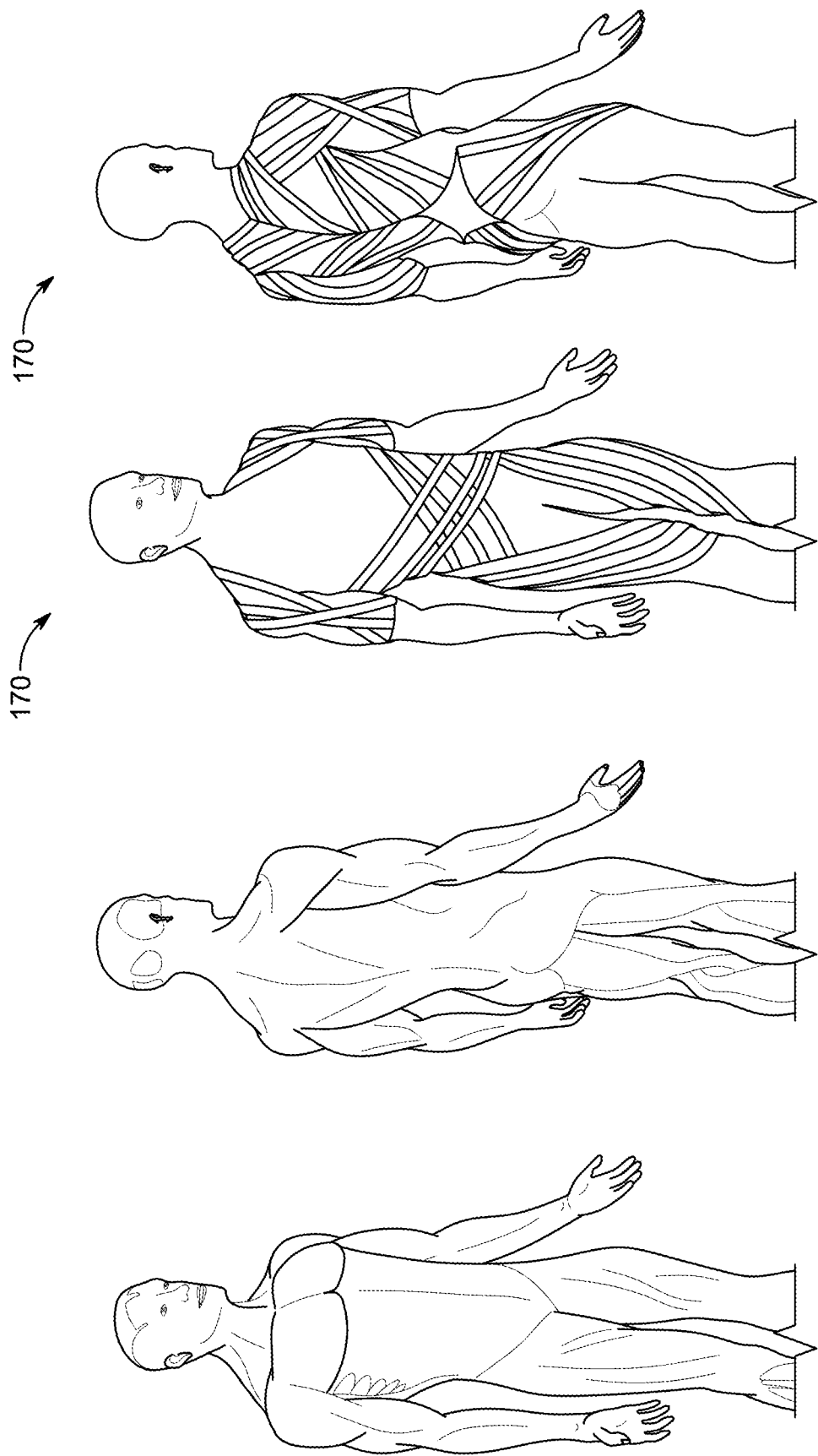

EXOSUIT SYSTEMS AND METHODS FOR POSTURE SESSION SEGMENTATION AND BIOMECHANICAL FEEDBACK

CROSS-REFERENCE TO RELATED APPLICATION

This application claims priority to U.S. Provisional Patent Application No. 62/668,262, filed May 8, 2018, which is incorporated by reference in its entirety.

TECHNICAL FIELD

This disclosure relates generally to the field of data analytics, and more specifically to systems and methods for efficiently monitoring posture.

BACKGROUND

Wearable robotic systems have been developed for augmentation of humans' natural capabilities, or to replace functionality lost due to injury or illness. Sensors integrated into the wearable robotic can generating large volumes of new types of data, spurring a new revolution in data science and services. Some of this data can relate to posture.

SUMMARY

Systems and methods for monitoring posture of a user wearing an exosuit are discussed herein. Exosuits worn by users can monitor several movement factors that characterize the user's movements and posture. The user's posture is identified and analyzed, and feedback is provided to the user based on the analyzed posture.

In one embodiment, an exosuit system is provided that can include an exosuit having a base layer, a power layer, and a plurality of sensors, wherein the exosuit is operative to provide the plurality of assistive movements; and control circuitry coupled to the power layer and the plurality of sensors. The control circuitry can be operative to receive data from the plurality of sensors during an exosuit use period, identify segments of relatively high user activity and segments of relatively low user activity within the received data that occurred during the exosuit use period, wherein the segments of relatively low user activity occur in between the segments of relatively high user activity, analyze data associated with the segments of relatively low user activity to obtain a plurality of posture sessions performed by a user of the exosuit during the exosuit use period, wherein each of the plurality of posture sessions specifies a posture position comprising forward/backward lean angle and a left/right lean angle, and provide feedback via the exosuit based on the plurality of posture sessions.

In another embodiment, a method for using an exosuit having a base layer, a power layer, and a plurality of sensors is provided. The method can include receiving data from the plurality of sensors during an exosuit use period, identifying segments of relatively high user activity and segments of relatively low user activity within the received data that occurred during the exosuit use period, wherein the segments of relatively low user activity occur in between the segments of relatively high user activity, analyzing data associated with the segments of relatively low user activity to obtain a plurality of posture sessions performed by a user of the exosuit during the exosuit use period, wherein each of the plurality of posture sessions includes a posture position and a posture duration, and providing feedback via the exosuit based on the posture position and the posture duration.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIGS. 1A-1C show front, back, and side views of a base layer of an exosuit according to an embodiment;

FIGS. 1G and 1H show respective front and back views of a human male's musculature anatomy, according to an embodiment;

FIGS. 1I and 1J show front and side views of an illustrative exosuit having several power layer segments that approximate many of the muscles shown in FIGS. 1G and 1H, according to various embodiments;

DETAILED DESCRIPTION

Figures 1D, 1E, 1F:
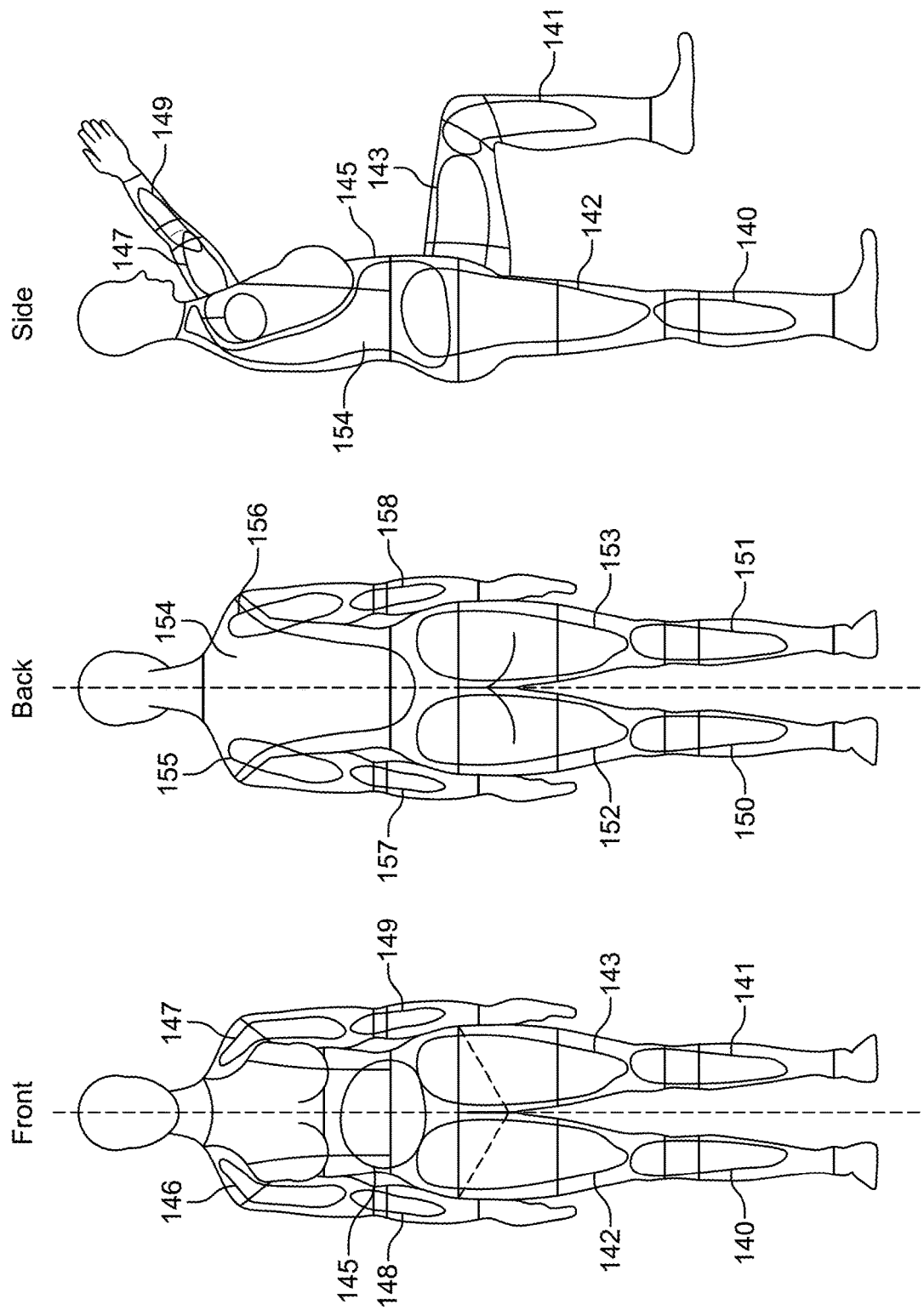
FIGS. 1D-1F show front, back, and side views, respectively, of a power layer according to an embodiment.

In the following description, numerous specific details are set forth regarding the systems, methods and media of the disclosed subject matter and the environment in which such systems, methods and media may operate, etc., in order to provide a thorough understanding of the disclosed subject matter. It can be apparent to one skilled in the art, however, that the disclosed subject matter may be practiced without such specific details, and that certain features, which are well known in the art, are not described in detail in order to avoid complication of the disclosed subject matter. In addition, it can be understood that the examples provided below are exemplary, and that it is contemplated that there are other systems, methods and media that are within the scope of the disclosed subject matter.

Embodiments discussed herein are inertial sensing data such as accelerometers, gyroscopes and magnetometers to be used to measure and monitor the biomechanical posture behaviors of individuals. The system and method can be worn in discrete form-factors or blended into garments or incorporated into an exosuit, and used to determine posture and activity states, and provide appropriate feedback to the user on their activity and posture behaviors. This is a new approach to segmenting and analyzing posture data and providing smarter feedback to each individual user.

In the descriptions that follow, an exosuit or assistive exosuit is a suit that is worn by a wearer on the outside of his or her body. It may be worn under the wearer's normal clothing, over their clothing, between layers of clothing, or may be the wearer's primary clothing itself. The exosuit may be supportive, assistive, resistive, and/or enchanting as it physically interacts with the wearer while performing particular activities, or can provide other functionality such as communication to the wearer through physical expressions to the body, engagement of the environment, or capturing of information from the wearer. In some embodiments, a powered exosuit system can include several subsystems, or layers. In some embodiments, the powered exosuit system can include more or less subsystems or layers. The subsystems or layers can include the base layer, stability layer, power layer, sensor and controls layer, a covering layer, and user interface/user experience (UI/UX) layer.

The base layer provides the interfaces between the exosuit system and the wearer's body. The base layer may be adapted to be worn directly against the wearer's skin, between undergarments and outer layers of clothing, over outer layers of clothing or a combination thereof, or the base layer may be designed to be worn as primary clothing itself. In some embodiments, the base layer can be adapted to be both comfortable and unobtrusive, as well as to comfortably and efficiently transmit loads from the stability layer and power layer to the wearer's body in order to provide the desired assistance. The base layer can typically comprise several different material types to achieve these purposes. Elastic materials may provide compliance to conform to the wearer's body and allow for ranges of movement. The innermost layer is typically adapted to grip the wearer's skin, undergarments or clothing so that the base layer does not slip as loads are applied. Substantially inextensible materials may be used to transfer loads from the stability layer and power layer to the wearer's body. These materials may be substantially inextensible in one axis, yet flexible or extensible in other axes such that the load transmission is along preferred paths. The load transmission paths may be optimized to distribute the loads across regions of the wearer's body to minimize the forces felt by the wearer, while providing efficient load transfer with minimal loss and not causing the base layer to slip. Collectively, this load transmission configuration within the base layer may be referred to as a load distribution member. Load distribution members refer to flexible elements that distribute loads across a region of the wearer's body. Examples of load distribution members can be found in International Patent Publication No. WO 2016/138264, titled "Flexgrip," the contents of which are incorporated herein by reference.

The load distribution members may incorporate one or more load lines or catenary curves to distribute loads across the wearer's body. Multiple load distribution members or catenary curves may be joined with pivot points, such that as loads are applied to the structure, the arrangement of the load distribution members pivots tightens or constricts on the body to increase the gripping strength. Compressive elements such as battens, rods, or stays may be used to transfer loads to different areas of the base layer for comfort or structural purposes. For example, a power layer component may terminate in the middle back due to its size and orientation requirements, however the load distribution members that anchor the power layer component may reside on the lower back. In this case, one or more compressive elements may transfer the load from the power layer component at the middle back to the load distribution member at the lower back.

The load distribution members may be constructed using multiple fabrication and textile application techniques. For example, the load distribution member can be constructed from a layered woven 45°/90° with bonded edge, spandex tooth, organza (poly) woven 45°/90° with bonded edge, organza (cotton/silk) woven 45°/90°, and Tyvek (non-woven). The load distribution member may be constructed using knit and lacing or horse hair and spandex tooth. The load distribution member may be constructed using channels and/or laces.

The base layer may include a flexible underlayer that is constructed to compress against a portion of the wearer's body, either directly to the skin, or to a clothing layer, and also provides a relatively high grip surface for one or more load distribution members to attach thereto. The load distribution members can be coupled to the underlayer to facilitate transmission of shears or other forces from the members, via the flexible underlayer, to skin of a body segment or to clothing worn over the body segment, to maintain the trajectories of the members relative to such a body segment, or to provide some other functionality. Such a flexible underlayer could have a flexibility and/or compliance that differs from that of the member (e.g., that is less than that of the members, at least in a direction along the members), such that the member can transmit forces along their length and evenly distribute shear forces and/or pressures, via the flexible underlayer, to skin of a body segment to which a flexible body harness is mounted.

Further, such a flexible underlayer can be configured to provide additional functionality. The material of the flexible underlayer could include anti-bacterial, anti-fungal, or other agents (e.g., silver nanoparticles) to prevent the growth of microorganisms. The flexible underlayer can be configured to manage the transport of heat and/or moisture (e.g., sweat) from a wearer to improve the comfort and efficiency of activity of the wearer. The flexible underlayer can include straps, seams, hook-and-loop fasteners, clasps, zippers, or other elements configured to maintain a specified relationship between elements of the load distribution members and aspects of a wearer's anatomy. The underlayer can additionally increase the ease with which a wearer can don and/or doff the flexible body harness and/or a system (e.g., a flexible exosuit system) or garment that includes the flexible body harness. The underlayer can additionally be configured to protect the wearer from ballistic weapons, sharp edges, shrapnel, or other environmental hazards (by including, e.g., panels or flexible elements of para-aramid or other high-strength materials).

The base layer can additionally include features such as size adjustments, openings and electro-mechanical integration features to improve ease of use and comfort for the wearer.

Size adjustment features permit the exosuit to be adjusted to the wearer's body. The size adjustments may allow the suit to be tightened or loosened about the length or circumference of the torso or limbs. The adjustments may comprise lacing, the Boa system, webbing, elastic, hook-and-loop or other fasteners. Size adjustment may be accomplished by the load distribution members themselves, as they constrict onto the wearer when loaded. In one example, the torso circumference may be tightened with corset-style lacing, the legs tightened with hook-and-loop in a double-back configuration, and the length and shoulder height adjusted with webbing and tension-lock fasteners such as cam-locks, D-rings or the like. The size adjustment features in the base layer may be actuated by the power layer to dynamically adjust the base layer to the wearer's body in different positions, in order to maintain consistent pressure and comfort for the wearer. For example, the base layer may be required to tighten on the thighs when standing, and loosen when sitting such that the base layer does not excessively constrict the thighs when seated. The dynamic size adjustment may be controlled by the sensor and controls layer, for example by detecting pressures or forces in the base layer and actuating the power layer to consistently attain the desired force or pressure. This feature does not necessarily cause the suit to provide physical assistance, but can create a more comfortable experience for the wearer, or allow the physical assistance elements of the suit to perform better or differently depending on the purpose of the movement assistance.

Opening features in the base layer may be provided to facilitate donning (putting the exosuit on) and doffing (taking the exosuit off) for the wearer. Opening features may comprise zippers, hook-and-loop, snaps, buttons or other textile fasteners. In one example, a front, central zipper provides an opening feature for the torso, while hook-and-loop fasteners provide opening features for the legs and shoulders. In this case, the hook-and-loop fasteners provide both opening and adjustment features. In other examples, the exosuit may simply have large openings, for example around the arms or neck, and elastic panels that allow the suit to be donned and doffed without specific closure mechanisms. A truncated load distribution member may be simply extended to tighten on the wearer's body. Openings may be provided to facilitate toileting so the user can keep the exosuit on, but only have to remove or open a relatively small portion to use the bathroom.

Electro-mechanical integration features attach components of the stability layer, power layer and sensor and controls layer into the base layer for integration into the exosuit. The integration features may be for mechanical, structural, comfort, protective or cosmetic purposes. Structural integration features anchor components of the other layers to the base layer. For the stability and power layers, the structural integration features provide for load-transmission to the base layer and load distribution members, and may accommodate specific degrees of freedom at the attachment point. For example, a snap or rivet anchoring a stability or power layer element may provide both load transmission to the base layer, as well as a pivoting degree of freedom. Stitched, adhesive, or bonded anchors may provide load transmission with or without the pivoting degree of freedom. A sliding anchor, for example along a sleeve or rail, may provide a translational degree of freedom. Anchors may be separable, such as with snaps, buckles, magnets, clasps, hooks, or any other suitable closure mechanism; or may be inseparable, such as with stitching, adhesives or other bonding. Size adjustment features as described above may allow adjustment and customization of the stability and power layers, for example to adjust the tension of spring or elastic elements in the passive layer, or to adjust the length of actuators in the power layer.

Other integration features such as loops, pockets, and mounting hardware may simply provide attachment to components that do not have significant load transmission requirements, such as batteries, circuit boards, sensors, or cables. Components that exist as gravitation weight can be transmitted into support grips, for example, the load line on the outseam. In some cases, components may be directly integrated into textile components of the base layer. For example, cables or connectors may include conductive elements that are directly woven, bonded or otherwise integrated into the base layer.

Electromechanical integration features may also protect or cosmetically hide components of the stability, power or sensor and controls layers. Elements of the stability layer (e.g. elastic bands or springs), power layer (e.g. flexible linear actuators or twisted string actuators) or sensor and controls layer (e.g. cables) may travel through sleeves, tubes, or channels integrated into the base layer, which can both conceal and protect these components. The sleeves, tubes, or channels may also permit motion of the component, for example during actuation of a power layer element. The sleeves, channels, or tubes may comprise resistance to collapse, ensuring that the component remains free and uninhibited within.

Enclosures, padding, fabric coverings, or the like may be used to further integrate components of other layers into the base layer for cosmetic, comfort, thermal regulation, or protective purposes. For example, components such as motors, batteries, cables, or circuit boards may be housed within an enclosure, fully or partially covered or surrounded in padded material such that the components do not cause discomfort to the wearer, are visually unobtrusive and integrated into the exosuit, and are protected from the environment. Opening and closing features may additionally provide access to these components for service, removal, or replacement.

In some cases—particularly for exosuits configurable for either provisional use or testing—a tether may allow for some electronic and mechanical components to be housed off the suit. In one example, electronics such as circuit boards and batteries may be over-sized, to allow for added configurability or data capture. If the large size of these components makes it undesirable to mount them on the exosuit, they could be located separately from the suit and connected via a physical or wireless tether. Larger, over-powered motors may be attached to the suit via flexible drive linkages that allow actuation of the power layer without requiring large motors to be attached to the suit. Such over-powered configurations allow optimization of exosuit parameters without constraints requiring all components to be attached or integrated into the exosuit.

Electro-mechanical integration features may also include wireless communication. For example, one or more power layer components may be placed at different locations on the exosuit. Rather than utilizing physical electrical connections to the sensors and controls layer, the sensor and controls layer may communicate with the one or more power layer components via wireless communication protocols such as Bluetooth, ZigBee, ultrawide band, or any other suitable communication protocol. This may reduce the electrical interconnections required within the suit. Each of the one or more power layer components may additionally incorporate a local battery such that each power layer component or group of power layer components are independently powered units that do not require direct electrical interconnections to other areas of the exosuit.

The stability layer provides passive mechanical stability and assistance to the wearer. The stability layer comprises one or more passive (non-powered) spring or elastic elements that generate forces or store energy to provide stability or assistance to the wearer. An elastic element can have an un-deformed, least-energy state. Deformation, e.g. elongation, of the elastic element stores energy and generates a force oriented to return the elastic element toward its least-energy state. For example, elastic elements approximating hip flexors and hip extensors may provide stability to the wearer in a standing position. As the wearer deviates from the standing position, the elastic elements are deformed, generating forces that stabilize the wearer and assist maintaining the standing position. In another example, as a wearer moves from a standing to seated posture, energy is stored in one or more elastic elements, generating a restorative force to assist the wearer when moving from the seated to standing position. Similar passive, elastic elements may be adapted to the torso or other areas of the limbs to provide positional stability or assistance moving to a position where the elastic elements are in their least-energy state.

Elastic elements of the stability layer may be integrated to parts of the base layer or be an integral part of the base layer. For example elastic fabrics containing spandex or similar materials may serve as a combination base/stability layer. Elastic elements may also include discrete components such as springs or segments of elastic material such as silicone or elastic webbing, anchored to the base layer for load transmission at discrete points, as described above.

The stability layer may be adjusted as described above, both to adapt to the wearer's size and individual anatomy, as well as to achieve a desired amount of pre-tension or slack in components of the stability layer in specific positions. For example, some wearers may prefer more pre-tension to provide additional stability in the standing posture, while others may prefer more slack, so that the passive layer does not interfere with other activities such as ambulation.

The stability layer may interface with the power layer to engage, disengage, or adjust the tension or slack in one or more elastic elements. In one example, when the wearer is in a standing position, the power layer may pre-tension one or more elastic elements of the stability layer to a desired amount for maintaining stability in that position. The pre-tension may be further adjusted by the power layer for different positions or activities. In some embodiments, the elastic elements of the stability layer should be able to generate at least 5 lbs force; preferably at least 50 lbs force when elongated.

The power layer can provide active, powered assistance to the wearer, as well as electromechanical clutching to maintain components of the power or stability layers in a desired position or tension. The power layer can include one or more flexible linear actuators (FLA). An FLA is a powered actuator capable of generating a tensile force between two attachment points, over a give stroke length. An FLA is flexible, such that it can follow a contour, for example around a body surface, and therefore the forces at the attachment points are not necessarily aligned. In some embodiments, one or more FLAs can include one or more twisted string actuators. In the descriptions that follow, FLA refers to a flexible linear actuator that exerts a tensile force, contracts or shortens when actuated. The FLA may be used in conjunction with a mechanical clutch that locks the tension force generated by the FLA in place so that the FLA motor does not have to consume power to maintain the desired tension force. Examples of such mechanical clutches are discussed below. In some embodiments, FLAs can include one or more twisted string actuators or flexdrives, as described in further detail in U.S. Pat. No. 9,266,233, titled "Exosuit System," the contents of which are incorporated herein by reference. FLAs may also be used in connection with electrolaminate clutches, which are also described in the U.S. Pat. No. 9,266,233. The electrolaminate clutch (e.g., clutches configured to use electrostatic attraction to generate controllable forces between clutching elements) may provide power savings by locking a tension force without requiring the FLA to maintain the same force.

The powered actuators, or FLAs, are arranged on the base layer, connecting different points on the body, to generate forces for assistance with various activities. The arrangement can often approximate the wearer's muscles, in order to naturally mimic and assist the wearer's own capabilities. For example, one or more FLAs may connect the back of the torso to the back of the legs, thus approximating the wearer's hip extensor muscles. Actuators approximating the hip extensors may assist with activities such as standing from a seated position, sitting from a standing position, walking, or lifting. Similarly, one or more actuators may be arranged approximating other muscle groups, such as the hip flexors, spinal extensors, abdominal muscles or muscles of the arms or legs.

The one or more FLAs approximating a group of muscles are capable of generating at least 10 lbs over at least a ½ inch stroke length within 4 seconds. In some embodiments, one or more FLAs approximating a group of muscles may be capable of generating at least 250 lbs over a 6-inch stroke within ½ second. Multiple FLAs, arranged in series or parallel, may be used to approximate a single group of muscles, with the size, length, power, and strength of the FLAs optimized for the group of muscles and activities for which they are utilized.

The sensor and controls layer captures data from the suit and wearer, utilizes the sensor data and other commands to control the power layer based on the activity being performed, and provides suit and wearer data to the UX/UI layer for control and informational purposes.

Sensors such as encoders or potentiometers may measure the length and rotation of the FLAs, while force sensors measure the forces applied by the FLAs. Inertial measurement units (IMUs) measure and enable computation of kinematic data (positions, velocities and accelerations) of points on the suit and wearer. These data enable inverse dynamics calculations of kinetic information (forces, torques) of the suit and wearer. Electromyographic (EMG) sensors may detect the wearer's muscle activity in specific muscle groups. Electronic control systems (ECSs) on the suit may use parameters measured by the sensor layer to control the power layer. Data from the IMUs may indicate both the activity being performed, as well as the speed and intensity. For example, a pattern of IMU or EMG data may enable the ECS to detect that the wearer is walking at a specific pace. This information then enables the ECS, utilizing the sensor data, to control the power layer in order to provide the appropriate assistance to the wearer. Stretchable sensors may be used as a strain gauge to measure the strain of the elements in the stability layer, and thereby predict the forces in the elastic elements of the stability layer. Stretchable sensors may be embedded in the base layer or grip layer and used to measure the motion of the fabrics in the base layer and the motion of the body.

Data from the sensor layer may be further provided to the UX/UI layer, for feedback and information to the wearer, caregivers or service providers.

The UX/UI layer comprises the wearer's and others' interaction and experience with the exosuit system. This layer includes controls of the suit itself such as initiation of activities, as well as feedback to the wearer and caregivers. A retail or service experience may include steps of fitting, calibration, training and maintenance of the exosuit system.

Other UX/UI features may include additional lifestyle features such as electronic security, identity protection and health status monitoring.

The assistive exosuit can have a user interface for the wearer to instruct the suit which activity is to be performed, as well as the timing of the activity. In one example, a user may manually instruct the exosuit to enter an activity mode via one or more buttons, a keypad, or a tethered device such as a mobile phone. In another example, the exosuit may detect initiation of an activity from the sensor and controls layer, as described previously. In yet another example, the user may speak a desired activity mode to the suit, which can interpret the spoken request to set the desired mode. The suit may be pre-programmed to perform the activity for a specific duration, until another command is received from the wearer, or until the suit detects that the wearer has ceased the activity. The suit may include cease activity features that, when activated, cause the suit to cease all activity. The cease activity features can take into account the motion being performed, and can disengage in a way that takes into account the user's position and motion, and safely returns the user to an unloaded state in a safe posture.

The exosuit may have a UX/UI controller that is defined as a node on another user device, such as a computer or mobile smart phone. The exosuit may also be the base for other accessories. For example, the exosuit may include a cell phone chip so that the suit may be capable of receiving both data and voice commands directly similar to a cell phone, and can communicate information and voice signals through such a node. The exosuit control architecture can be configured to allow for other devices to be added as accessories to the exosuit. For example, a video screen may be connected to the exosuit to show images that are related to the use of the suit. The exosuit may be used to interact with smart household devices such as door locks or can be used to turn on smart televisions and adjust channels and other settings. In these modes, the physical assist of the suit can be used to augment or create physical or haptic experiences for the wearer that are related to communication with these devices. For instance, an email could have a pat on the back as a form of physical emoji that when inserted in the email causes the suit to physically tap the wearer or perform some other type of physical expression to the user that adds emphasis to the written email.

The exosuit may provide visual, audio, or haptic feedback or cues to inform the user of various exosuit operations. For example, the exosuit may include vibration motors to provide haptic feedback. As a specific example, two haptic motors may be positioned near the front hip bones to inform the user of suit activity when performing a sit-to-stand assistive movement. In addition, two haptic motors may be positioned near the back hip bones to inform the user of suit activity when performing a stand-to-sit assistive movement. The exosuit may include one or more light emitting diodes (LEDs) to provide visual feedback or cues. For example, LEDS may be placed near the left and/or right shoulders within the peripheral vision of the user. The exosuit may include a speaker or buzzer to provide audio feedback or cues.

In other instances, the interaction of the FLA's with the body through the body harness and otherwise can be used as a form of haptic feedback to the wearer, where changes in the timing of the contraction of the FLA's can indicate certain information to the wearer. For instance, the number or strength of tugs of the FLA on the waist could indicate the amount of battery life remaining or that the suit has entered a ready state for an impending motion.

The control of the exosuit may also be linked to the sensors that are measuring the movement of the wearer, or other sensors, for instance on the suit of another person, or sensors in the environment. The motor commands described herein may all be activated or modified by this sensor information. In this example, the suit can exhibit its own reflexes such that the wearer, through intentional or unintentional motions, cues the motion profile of the suit. When sitting, for further example, the physical movement of leaning forward in the chair, as if to indicate an intention to stand up, can be sensed by the suit IMU's and be used to trigger the sit to stand motion profile. In one embodiment, the exosuit may include sensors (e.g., electroencephalograph (EEG) sensor) that are able to monitor brain activity may be used to detect a user's desire to perform a particular movement. For example, if the user is sitting down, the EEG sensor may sense the user's desire to stand up and cause the exosuit to prime itself to assist the user in a sit-to-stand assistive movement.

The suit may make sounds or provide other feedback, for instance through quick movements of the motors, as information to the user that the suit has received a command or to describe to the user that a particular motion profile can be applied. In the above reflex control example, the suit may provide a high pitch sound and/or a vibration to the wearer to indicate that it is about to start the movement. This information can help the user to be ready for the suit movements, improving performance and safety. Many types of cues are possible for all movements of the suit.

Control of the suit includes the use of machine learning techniques to measure movement performance across many instances of one or of many wearers of suits connected via the internet, where the calculation of the best control motion for optimizing performance and improving safety for any one user is based on the aggregate information in all or a subset of the wearers of the suit. The machine learning techniques can be used to provide user specific customization for exosuit assistive movements. For example, a particular user may have an abnormal gait (e.g., due to a car accident) and thus is unable to take even strides. The machine learning may detect this abnormal gait and compensate accordingly for it.

FIGS. 1A-1C show front, back, and side views of a base layer 100 of an exosuit according to an embodiment. Base layer 100 may be worn as a single piece or as multiple pieces. As shown, base layer 100 is shown to represent multiple pieces that can serve as load distribution members (LDMs) for the power layer (shown in FIGS. 1D-1F). Base layer 100 and any LDMs thereof can cover or occupy any part of the human body as desired. The LDMs shown in FIGS. 1A-1C are merely illustrative of a few potential locations and it should be appreciated that additional LDMs may be added or certain LDMs may be omitted.

Base layer 100 can include calf LDMs 102 and 104 that are secured around the calf region or lower leg portion of the human. Calf LDMs 102 and 104 are shown to be positioned between the knees and the ankles, but this is merely illustrative. If desired, calf LDM 102 and 104 can also cover the foot and ankle and/or the knee.

Base layer 100 can include thigh LDMs 106 and 108 that are secured around the thigh region of the human. Thigh LDMs 106 and 108 are shown to be positioned between the knees and an upper region of the thighs. In some embodiments, thigh LDMs 106 and 108 and calf LDMs 102 and 104, respectively, may be merged together to form leg LDMs that cover the entirety of the legs and/or feet.

Base layer 100 can include hip LDM 110 that is secured around a hip region of the human. LDM 110 may be bounded such that it remains positioned above the toileting regions of the human. Such bounding may make toileting relatively easy for the human as he or she would be not be required to remove base layer 100 to use the bathroom. In some embodiments, LDM 110 may be attached to thigh LDMs 106 and 108, but the toileting regions may remain uncovered. In another embodiment, a removable base layer portion may exist between LDM 100 and thigh LDMS 106 and 108.

Base layer 100 can include upper torso LDM 112 that is secured around an upper torso region of the human. Upper torso LDM 112 may include waist LDM 113, back LDM 114, shoulder LDM 115, and shoulder strap LDMs 116. Waist LDM 113, back LDM 114, shoulder LDM 115, and shoulder strap LDMs 116 may be integrally formed to yield upper torso LDM 112. In some embodiments, a chest LDM (not shown) may also be integrated into upper torso LDM 112. Female specific exosuits may have built in bust support for the chest LDM.

Base layer 100 can include upper arm LDMs 120 and 122 and lower arm LDMs 124 and 126. Upper arm LDMs 120 and 122 may be secured around bicep/triceps region of the arm and can occupy space between the shoulder and the elbow. Lower arm LDMs 124 and 126 may be secured around the forearm region of the arm and can occupy the space between the elbow and the wrist. If desired, upper arm LDM 120 and lower arm LDM 124 may be integrated to form an arm LDM, and upper arm LDM 122 and lower arm LDM 126 may be integrated to form another arm LDM. In some embodiments, arm LDMS 120, 122, 124, and 126 may form part of upper torso LDM 112.

Base layer 100 can include gluteal/pelvic LDM 128 that is secured the gluteal and pelvic region of the human. LDM 128 may be positioned between thigh LDMs 106 and 108 and hip LDM 110. LDM 128 may have removable portions such as buttoned or zippered flaps that permit toileting. Although not shown in FIGS. 1A-1C, LDMs may exist for the feet, toes, neck, head, hands, fingers, elbows, or any other suitable body part.

As explained above, the LDMs may serve as attachment points for components of the power layer. In particular, the components that provide muscle assistance movements typically need to be secured in at least two locations on the body. This way, when the flexible linear actuators are engaged, the contraction of the actuator can apply a force between the at least two locations on the body. With LDMs strategically placed around the body, the power layer can also be strategically placed thereon to provide any number of muscle assistance movements. For example, the power layer may be distributed across different LDMs or within different regions of the same LDM to approximate any number of different muscles or muscle groups. The power layer may approximate muscle groups such as the abdominals, adductors, dorsal muscles, shoulders, arm extensors, wrist extensors, gluteals, arm flexors, wrist flexors, scapulae fixers, thigh flexors, lumbar muscles, surae, pectorals, quadriceps, and trapezii. The power layer may also apply forces along paths that are not representative of biological muscle groups. For example, the power layer may wrap around the knee for stability and support.

FIGS. 1D-1F show front, back, and side views, respectively, of a power layer according to an embodiment. The power layer is shown as multiple segments distributed across and within the various LDMs. As shown, the power layer can include power layer segments 140-158. Each of power layer segments can include any number of flexible linear actuators. Some of the power layer segments may exist solely on the anterior side of the body, exist solely on the posterior side, start on the anterior side and wrap around to the posterior side, start on the posterior side and wrap around to the anterior side, or wrap completely around a portion of the body. Power layer segment (PLS) 140 may be secured to LDM 102 and LDM 106, and PLS 141 may be secured to LDM 104 and LDM 108. PLS 142 may be secured to LDM 106 and LDM 110 and/or LDM 114, and PLS 143 may be secured to LDM 108 and LDM 110 and/or LDM 114. PLS 145 may be secured to LDM 110 and LDM 113 and/or to LDM 114 or LDM 128. PLS 146 may be secured to LDM 115 and LDM 120, and PLS 147 may be secured to LDM 115 and LDM 122. PLS 148 may be secured to LDM 120 and LDM 124, and PLS 149 may be secured to LDM 122 and LDM 126.

PLS 150 may be secured to LDM 104 and LDM 108, and PLS 151 may be secured to LDM 102 and LDM 106. PLS 152 may be secured to LDM 106 and LDM 110 and/or to LDM 113, and PLS 153 may be secured to LDM 108 and LDM 110 and/or LDM 113. PLS 154 may be secured to LDM 112 and LDM 110. PLS 155 may be secured to LDM 112 and LDM 120, and PLS 156 may be secured to LDM 112 and LDM 122. PLS 157 may be secured to LDM 120 and LDM 124, and PLS 158 may be secured to LDM 122 and LDM 126.

It should be appreciated that the power layer segments are merely illustrative and that additional power layer segments may be added or that some segments may be omitted. In addition, the attachment points for the power layer segments are merely illustrative and that other attachment points may be used.

The human body has many muscles, including large and small muscles that are arranged in all sorts of different configuration. For example, FIGS. 1G and 1H show respective front and back views of a human male's musculature anatomy, which shows many muscles. In particular, the abdominals, adductors, dorsal muscles, shoulders, arm extensors, wrist extensors, gluteals, arm flexors, wrist flexors, scapulae fixers, thigh flexors, lumbar muscles, pectorals, quadriceps, and trapezii are all shown. It should be understood that several muscles and tendons are not shown.

The LDMs may be designed so that they can accommodate different sizes of individuals who don the exosuit. For example, the LDMs may be adjusted to achieve the best fit. In addition the LDMs are designed such that the location of the end points and the lines of action are co-located with the bone structure of the user in such a way that the flexdrive placement on the exosuit system are aligned with the actual muscle structure of the wearer for comfort, and the moment arms and forces generated by the flexdrive/exosuit system feel aligned with the forces generated by the wearer's own muscles.

FIGS. 1I and 1J show front and side views of illustrative exosuit 170 having several power layer segments that approximate many of the muscles shown in FIGS. 1G and 1H. The power layer segments are represented by the individual lines that span different parts of the body. These lines may represent specific flexible linear actuators or groups thereof that work together to form the power layer segments that are secured to the LDMs (not shown). As shown, the FLAs may be arrayed to replicate at least a portion of each of the abdominal muscles, dorsal muscles, shoulder muscles, arm extensor and flexor muscles, gluteal muscles, quadriceps muscles, thigh flexor muscles, and trapezii muscles. Thus, exosuit 170 exemplifies one of many possible different power layer segment arrangements that may be used in exosuits in accordance with embodiments discussed herein. These power layer segments are arranged so that the moment arms and forces generated feel like forces being generated by the user's own muscles, tendons, and skeletal structure. It should be appreciated that the power layer segments can be designed to approximate other muscles and tendons that are not shown in FIGS. 1G and 1H. Other possible power layer segment arrangements are illustrated and discussed below.

The power layer segments may be arranged such that they include opposing pairs or groups, similar to the way human muscles are arranged in opposing pairs or groups of muscles. That is, for a particular movement, the opposing pairs or groups can include protagonist and antagonist muscles. While performing the movement, protagonist muscles may perform the work, whereas the antagonist muscles provide stabilization and resistance to the movement. As a specific example, when a user is performing a curl, the biceps muscles may serve as the protagonist muscles and the triceps muscles may serve as the antagonist muscles. In this example, the power layer segments of an exosuit may emulate the biceps and triceps. When the biceps human muscle is pulling to bend the elbow, the exosuit triceps power layer segment can pull on the other side of the joint to resist bending of the elbow by attempting to extend it. The power layer segment can be, for example, either be a FLA operating alone to apply the force and motion, or a FLA in series with an elastic element. In the latter case, the human biceps would be working against the elastic element, with the FLA adjusting the length and thereby the resistive force of the elastic element.

Thus, by arranging the power layer segments in protagonist and antagonist pairs, the power layers segments can mimic or emulate any protagonist and antagonist pairs of the human anatomy musculature system. This can be used to enable exosuits to provide assistive movements, alignment movements, and resistive movements. For example, for any exercise movement requires activation of protagonist muscles, a subset of the power layer segments can emulate activation of antagonist muscles associated with that exercise movement to provide resistance.

The design flexibility of the LDMs and PLSs can enable exosuits to be constructed in accordance with embodiments discussed herein. Using exosuits, the power layer segments can be used to resist motion, assist motion, or align the user's form.

Figure 2A:
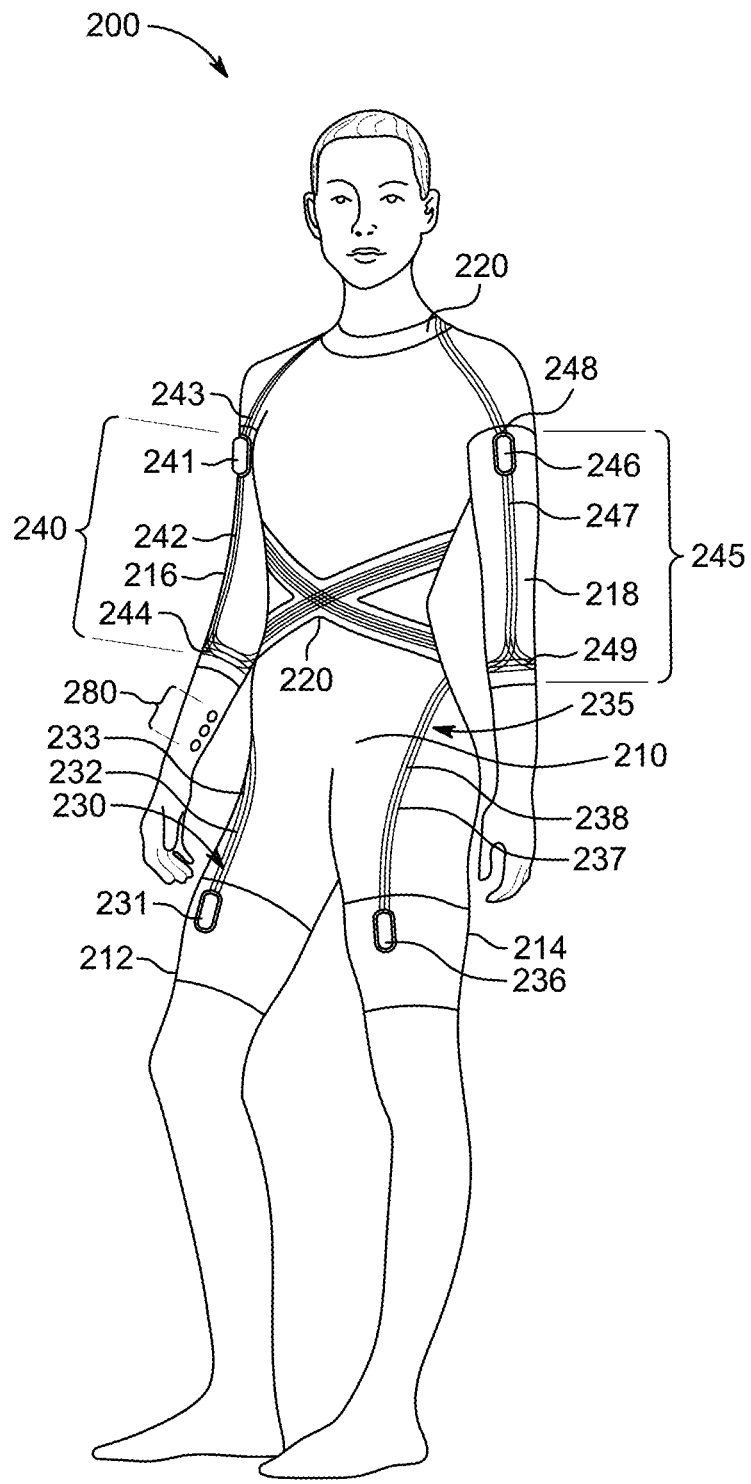
FIGS. 2A and 2B show front and back view of illustrative exosuit according to an embodiment.
Figure 2B:
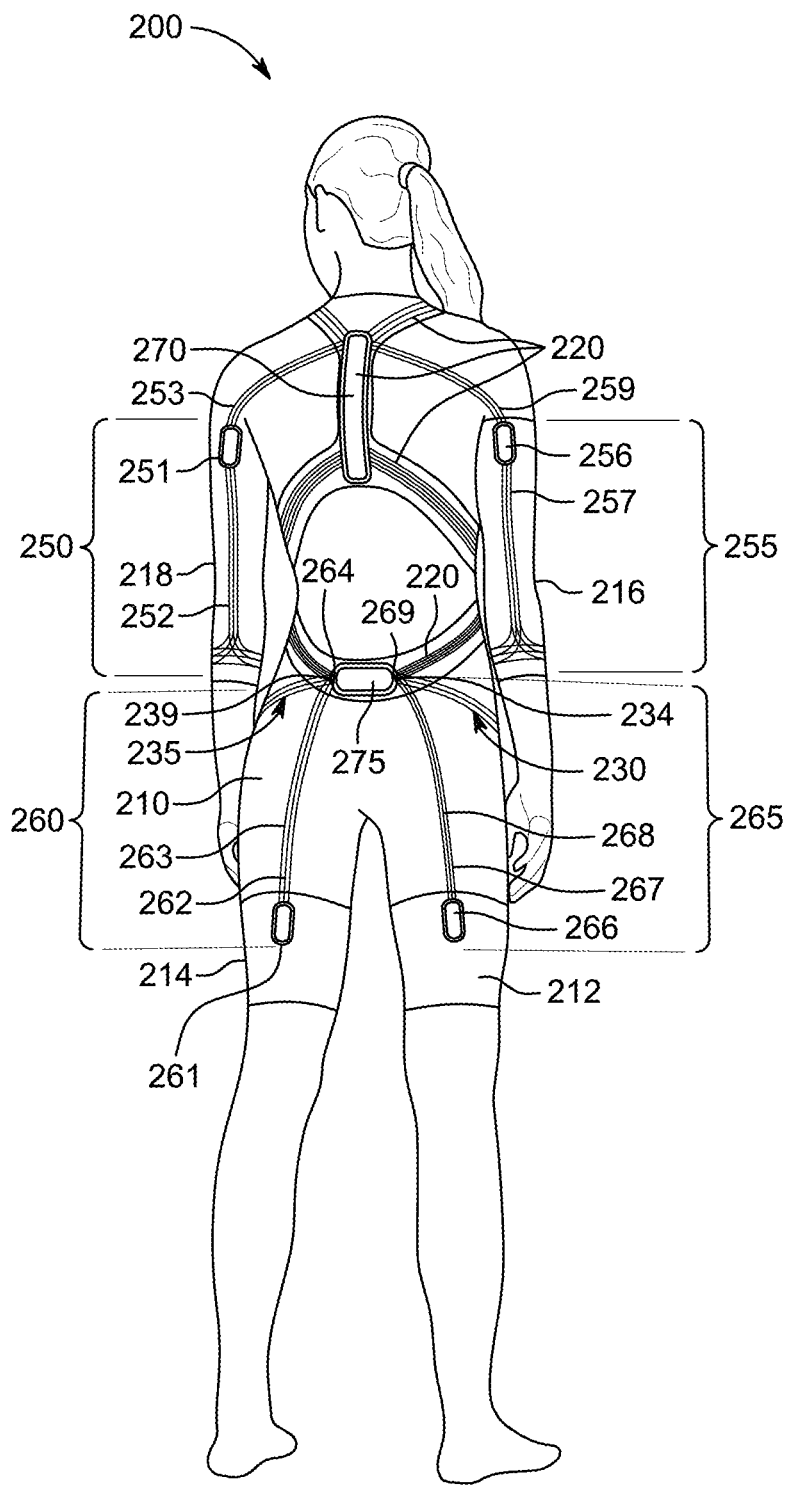

FIGS. 2A and 2B show front and back view of illustrative exosuit 200 according to an embodiment. Exosuit 200 may embody some or all of the base layer, stability layer, power layer, sensor and controls layer, a covering layer, and user interface/user experience (UI/UX) layer, as discussed above. In addition, exosuit 200 may represent one of many different specification implementations of the exosuit shown in FIGS. 1A-1F. Exosuit 200 can include base layer 210 with thigh LDMs 212 and 214, arm LDMs 216 and 218, and upper torso LDM 202. Thigh LDMs 212 and 214 may wrap around the thigh region of the human, and arm LDMs 216 and 218 may wrap around arm region (including the elbow) of the human. Upper torso LDM 220 may wrap around the torso and neck of the human as shown. In particular, LDM 220 may cross near the abdomen, abut the sacrum, cover a portion of the back, and extend around the neck.

Exosuit 200 can include PLSs 230 and 235 secured to thigh LDM 212 and 214 and upper torso LDM 220. PLSs 230 and 235 may provide leg muscle flexor movements. PLS 230 may include flexdrive subsystem 231, twisted string 232, and power/communication lines 233. Flexdrive subsystem 231 may include a motor, sensors, a battery, communications circuitry, and/or control circuitry. Twisted string 232 may be attached to flexdrive subsystem 231 and an attachment point 234 on LDM 220. Power/communications lines 233 may convey control signals and/or power to flexdrive subsystem 231. PLS 235 may include flexdrive subsystem 236, twisted string 237, and power/communication lines 238. Twisted string 237 may be attached to flexdrive subsystem 236 and attachment point 239.

Exosuit 200 can include PLSs 240 and 245 and PLSs 250 and 255 that are secured to LDMs 216, 218, and 220 (as shown). PLSs 240 and 245 may provide aim muscle flexor movements, and PLSs 250 and 255 may provide arm muscle extensor movements. PLS 240 may include flexdrive subsystem 241, twisted string 242, and power/communication lines 243. Twisted string 242 may be attached to flexdrive subsystem 241 and attachment point 244. Power/communication lines 243 may be coupled to power and communications module 270. PLS 245 may include flexdrive subsystem 246, twisted string 247, and power/communication lines 248. Twisted string 247 may be attached to flexdrive subsystem 246 and attachment point 249. Power/communication lines 248 may be coupled to power and communications module 270. PLS 250 may include flexdrive subsystem 251, twisted string 252, and power/communication lines 253. Twisted string 252 may be attached to flexdrive subsystem 251 and attachment point 254. Power/communication lines 253 may be coupled to power and communications module 270. PLS 250 may include flexdrive subsystem 256, twisted string 257, and power/communication lines 258. Twisted string 256 may be attached to flexdrive subsystem 256 and attachment point 259. Power/communication lines 258 may be coupled to power and communications module 270.

Exosuit 200 can include PLS 260 and 265 that are secured to thigh LDMs 212 and 214 and LDM 220. PLSs 260 and 265 may provide leg muscle flexor movements. PLS 260 may include flexdrive subsystem 261, twisted string 262, and power/communication lines 263. Twisted string 262 may be attached to flexdrive subsystem 261 and attachment point 264. Power/communication lines 263 may be coupled to power and communications module 275. PLS 266 may include flexdrive subsystem 266, twisted string 267, and power/communication lines 268. Twisted string 267 may be attached to flexdrive subsystem 266 and attachment point 269. Power/communication lines 263 may be coupled to power and communications module 275

Exosuit 200 is designed to assist, resist, align, or enhance movements being performed by the user of the suit. Exosuit 200 may include many sensors in various locations to provide data required by control circuitry to provide such movements. These sensors may be located anywhere on base layer 210 and be electrically coupled to power and communications lines (e.g., 233, 237, 243, 247, 253, 257, 263, 267, or other lines). The sensors may provide absolute position data, relative position data, accelerometer data, gyroscopic data, inertial moment data, strain gauge data, resistance data, or any other suitable data.

Exosuit 200 may include user interface 280 that enables the user to control the exosuit. For example, user interface 280 can include several buttons or a touch screen interface. User interface 280 may also include a microphone to receive user spoken commands User interface 280 may also include a speaker that can be used to playback voice recordings. Other user interface element such as buzzers (e.g., vibrating elements) may be strategically positioned around exosuit 200.

Exosuit 200 can include communications circuitry such as that contained in power and communications module 270 or 275 to communicate directly with a user device (e.g., a smartphone) or with the user device via a central server. The user may use the user device to select one or more movements he or she would like to perform, and upon selection of the one or more movements, exosuit 200 can the assist, resist, or align movement. The user device or exosuit 200 may provide real-time alignment guidance as to the user's performance of the movement, and exosuit 200 may provide resistance, alignment, or assistance to the movement.

An exosuit can be operated by electronic controllers disposed on or within the exosuit or in wireless or wired communication with the exosuit. The electronic controllers can be configured in a variety of ways to operate the exosuit and to enable functions of the exosuit. The electronic controllers can access and execute computer-readable programs that are stored in elements of the exosuit or in other systems that are in direct or indirect communications with the exosuit. The computer-readable programs can describe methods for operating the exosuit or can describe other operations relating to a exosuit or to a wearer of a exosuit.

Figure 3:
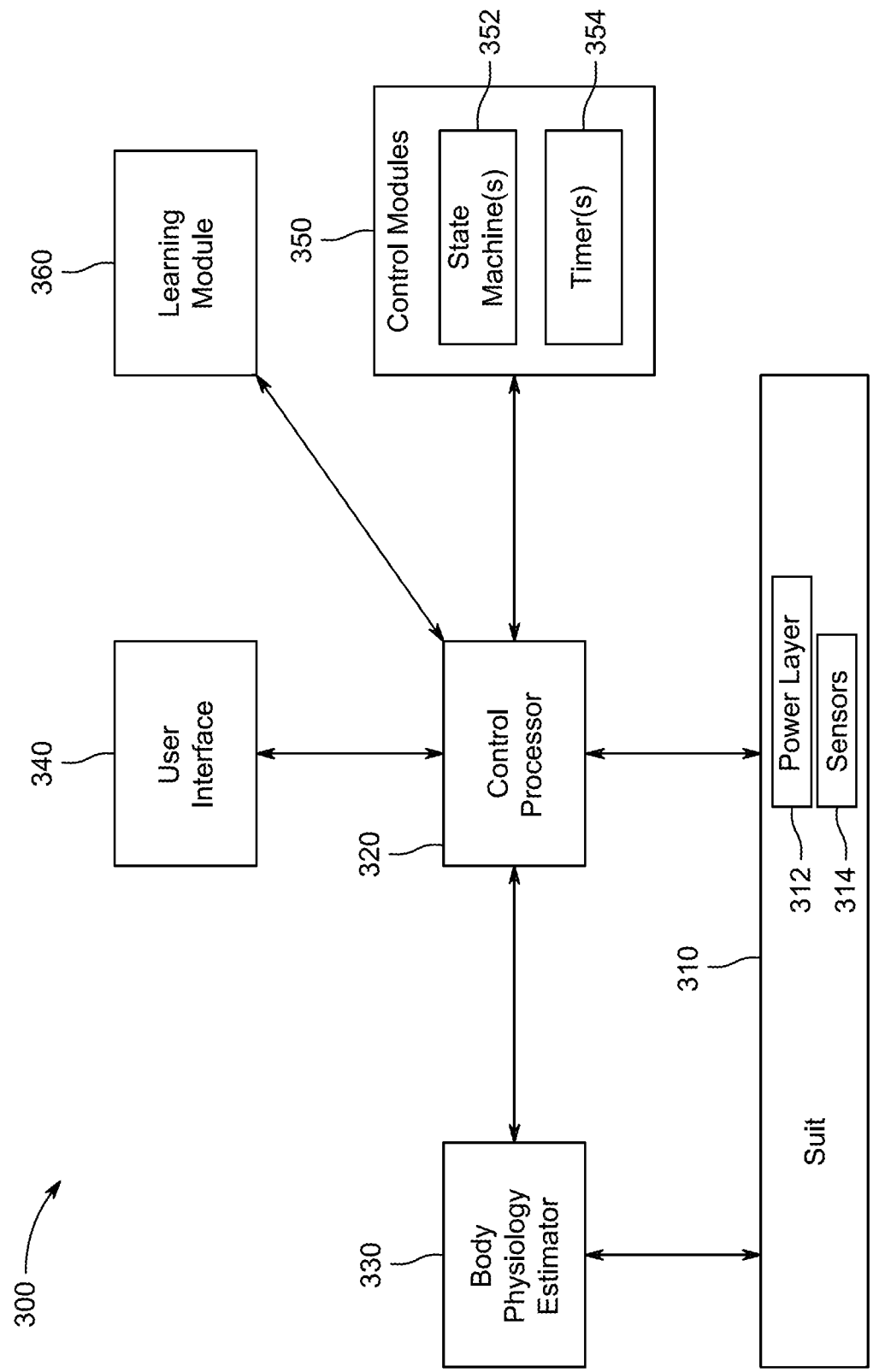
FIG. 3 shows an illustrative symbiosis exosuit system according to an embodiment.

FIG. 3 shows an illustrative symbiosis exosuit system 300 according to an embodiment. The symbiosis enables the exosuit to serve as an autonomous exosuit nervous system that mimics or emulates the nervous system of a lifeform such as a human being. That is, a nervous system is responsible for basic life functions (e.g., breathing, converting food into energy, and maintaining muscle balance) that are performed automatically without requiring conscious thought or input. The autonomous exosuit nervous system enables the exosuit to automatically provide assistance to the user when and where the user needs it without requiring intervention by the user. Exosuit system 300 can do this by tracking the user's body physiology and automatically controlling the suit to provide the anticipated or required support and/or assistance. For example, if a user has been standing for a prolonged period of time, one or more of the muscles being used to help the user stand may begin to tire, and a result, the user's body may exhibit signs of fatigue. Exosuit 300 can observe this muscle fatigue (e.g., due to observed physiological signs) and can automatically cause exosuit 300 to engage the appropriate power layers to compensate for the muscle fatigue.

Symbiosis of exosuit 300 may be expressed in different autonomy levels, where each autonomy level represents a degree to which physiological factors are observed and a degree to which suit assistance or movement actions are performed based on the observed physiological factors. For example, the symbiosis levels can range from a zero level of autonomy to absolute full level of autonomy, with one or more intermediate levels of autonomy. As metaphorical example, autonomous cars operate according to different levels, where each level represents a different ability for the car to self-drive. The symbiosis levels of exosuit operation can be stratified in a similar manner. In a zero level of autonomy, exosuit 300 may not monitor for any physiological cues, nor automatically engage any suit assistance or movement actions. Thus, in a zero level, the user may be required to provide user input to instruct the suit to perform a desired movement or assistance. In an absolute full level of autonomy, exosuit 300 may be able to observe and accurately analyze the observed physiological data (e.g., with 99 percent accuracy or more) and automatically execute the suit assistance or movement actions in a way expressly desired by the user. Thus, in the absolute full level, the exosuit seamlessly serves as an extension of the user's nervous system by automatically determining what the user needs and providing it.

The one or more intermediate levels of autonomy provide different observable physiological results that are accurate but do not represent the absolute nature of the absolute full level of autonomy. For example, the intermediate levels may represent that the exosuit is fully capable of autonomously performing certain actions (e.g., sit to stand) but not others. A corollary to this is ABS braking; the ABS braking system automatically figures out how best to stop the vehicle without requiring the user to pump the brakes or engage in any other activity other than stepping on the brake pedal. In the exosuit context, the exosuit knows when the user wishes to stand from a sitting position, the exosuit knows when the user wishes to perform the movement and engages the appropriate power layer segments to assist in the movement. The intermediate levels may also exist while the exosuit is learning about its user. Each user is different, and the physiological responses are therefore different and particular to each user. Therefore, the ability to discern the physiological cues and the assistance and movements made in response thereto may endure a learning curve before the suit is able to operate at the absolute full level.

FIG. 3 shows that exosuit system 300 can include suit 310, control processor 320, body physiology estimator 330, user interface 340, control modules 350, and learning module 360. Suit 310 can be any suitable exosuit (e.g., exosuit 200) and can include, among other things, power layer 312 and sensors 314. Control processor 320 may process instructions, pass data, and control the suit. Control processor 320 may be connected to suit 310, body physiology estimator 330, user interface 340, control modules 350, and learning module 360. Control processor 320 may provide signals to suit 310 to control, for example, operation of power layer 312.

Body physiology estimator 330 may receive data inputs from sensor 314, control processor 320, and other components if desired. Estimator 330 is operative to analyze the data to ascertain the physiology of the user. Estimator 330 may apply data analytics and statistics to the data to resolve physiological conditions of the user's body. For example, estimator 330 can determine whether the user is sitting, standing, leaning, laying down, laying down on a side, walking, running, jumping, performing exercise movements, playing sports, reaching, holding an object or objects, or performing any other static or active physiological event. The results may be provided to control modules 350, for example, via control processor 320.

Sensors 314 can include an accelerometer, gyroscope, magnetometer, altimeter sensor, EKG sensor, and any other suitable sensor. Sensors 314 may be integrated anywhere within the exosuit, though certain locations may be more preferred than others. The sensor can be placed near the waist, upper body, shoes, thigh, arms, wrists or head. In some embodiments, sensors can be embedded onto the equipment being used by the user. In some embodiments, the sensors can be contained external to the exosuit. For example, if worn on the wrist or arm of a worker, the device can be embedded into a watch, wrist band, elbow sleeve, or arm band. A second device may be used and clipped on the waist on the pelvis, or slipped into a pocket in the garment, embedded into the garment itself, back-brace, belt, hard hat, protective glasses or other personal protective equipment the worker is wearing. The device can also be an adhesive patch worn on the skin. Other form factors can also clip onto the shoe or embedded into a pair of socks or the shoe itself.

Control modules 350 can include various state machines 352 and timers 354 operative to control operation of suit 310 based on outputs supplied by estimator 330, inputs received via a user interface 340, and signals provided by control processor 320. Multiple state machines 352 may control operation of the suit. For example, a master state machine may be supported by multiple slave state machines. The slave state machines may be executed in response to a call from the master state machine. In addition, the slave state machines may execute specific assistance functions or movements. For example, each of a sit-to-stand assistance movement, stand-to sit movement, stretch movement, standing movement, walking movement, running movement, jumping movement, crouch movement, specific exercise movement, or any other movement may have its own slave state machine to control suit operation.

Learning module 360 may be operative to learn preferences, peculiarities, or other unique features of a particular user and feedback the learnings to body physiology estimator 330 and control module 350. In some embodiments, learning module 360 may use data analytics to learn about the user. For example, learning module 360 may learn that a particular user walks with a particular gait and cadence. The gait and cadence learnings can be used to modify state machines 352 that control walking for that user. In another embodiment, learning module 360 may incorporate user feedback received via user interface 340. For example, a user may go through an initial setup process whereby the user is instructed to perform a battery of movements and provide responses thereto so that state machines 352 and timers 354 are set to operate in accordance with the preferences of the user.

Figure 4:
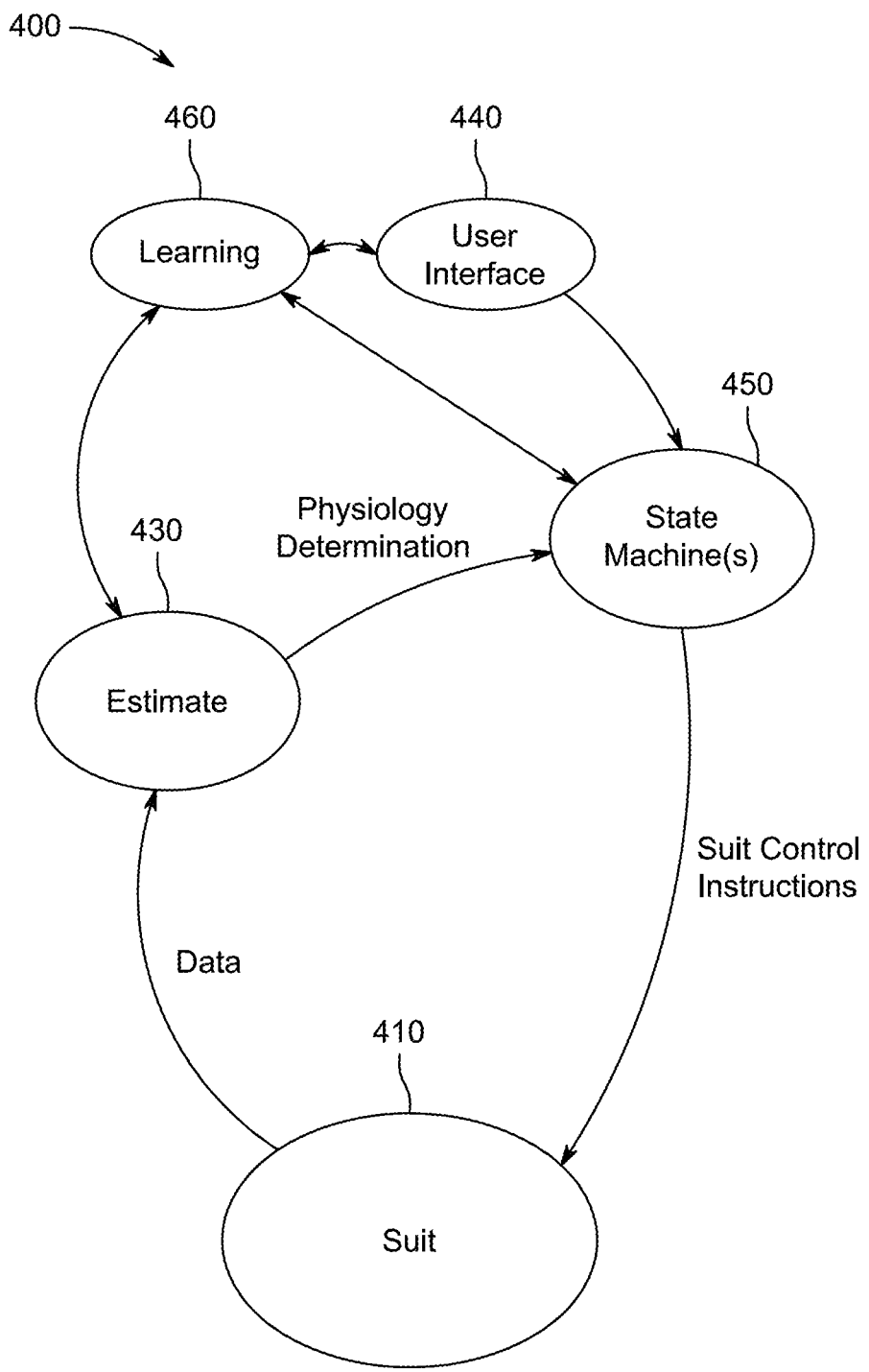
FIG. 4 shows illustrative process for implementing a symbiosis exosuit system according to an embodiment.

FIG. 4 shows illustrative process 400 for implementing symbiosis exosuit system 300 according to an embodiment. Process 400 includes suite 410, estimator 430, user interface 440, and state machines 450. Process 400 can be represented by a continuous feedback loop in which data is supplied from suit 410 to estimator 430, which provides a physiology determination to state machines 450, which uses the determination to generate suit control instructions that are provided to suit 410. User inputs received via user interface 440 may provide user specified controls that can instruct state machines 450 to execute a particular movement. The autonomous exosuit nervous system is implemented through the continuous feedback loop. The continuous feedback loop enables the autonomous exosuit nervous system to provide rapid response and control of exosuit 410. For example, if the user is sitting down, the estimator 430 can determine that the sitting position is the current physiological determination. Assume that the user reaches for something on a table. Such a movement may result in a movement that appears to be a sit-to-stand. In response to this movement, estimator 430 may register it as the start of a sit-to-stand physiological determination and instruct state machines 450 to initiate a sit-to-stand movement. This way, regardless of whether the user actually stands or sits back down, suit 410 is primed and ready to immediately perform the assistance movement. Further assume that the user sits back down (after having grabbed the item on the table). In response to initiation of the sit down movement, estimator 430 can make this determination as it is happening and instruct state machines 450 to cease the sit-to-stand operation. Thus, the continuous feedback loop provides real-time assessment and instantaneous suit controls in response to the user's immediate physiological needs, and not after.

In some embodiments, estimator 430 may be able to determine that the user is was attempting to reach something on the table while also performing the motion that includes at least the start of a sit to stand movement. Estimator 430 may be able to correlate the reaching motion with the sit-to-stand motion and decide that the user does not actually need to stand, but may require an appropriate amount of assist to reach the item. In this particular situation, state machine 450 may activate a power layer segment (e.g., a particular one of the hip extensors) to provide the user with the reach assistance.

Learning 460 can receive and provide data to estimator 430, user interface 440, and state machines 450. Learning 460 may be leveraged to update state machines 450 and/or estimator 430.

A method for posture detection and feedback system is described in U.S. Pat. No. 8,928,484, titled "SYSTEM AND METHOD FOR BIOMECHANICAL POSTURE DETECTION AND FEEDBACK", filed 12 Jul. 2013, the disclosure of which is incorporated by reference in its entirety.

The exosuit may autocalibrate its sensors each time one or more of the sensors detect motion or wakes up from a low power sleep mode. When the user begins walking, for example, the sensor and system can recognize a walking signal and then begins an auto-calibration sequence that generates a reference orientation frame to abstract sensor placement (and corresponding raw sensor data) from additional computation. A method for auto calibration is described in US Patent Publication no. 2017/0258374, titled "SYSTEM AND METHOD FOR AUTOMATIC POSTURE CALIBRATION", which is hereby incorporated in its entirety by this reference.

In addition to auto-calibration, all sensors that are part of the exosuit can be synchronized to the same time. This can be accomplished by connecting with each other, being connected via an onboard processor system, or with a peripheral device such as a smart phone or smart watch that has a reliable real-time clock.

After the auto-calibration sequence, the exosuit may determine the location of where each sensor is being worn on the body by analyzing unique location specific motion signatures. A method for automatic location detection has been described in US Patent Publication no. 2018/0264320, titled "SYSTEM AND METHOD FOR AUTOMATIC WEARABLE SENSOR LOCATION DETECTION FOR WEARABLE SENSORS," which is hereby incorporated in its entirety. When the sensor locations are determined (e.g., the specific locations and orientation of the sensors on the exosuit), the exosuit system can determine the appropriate location specific posture model. For example, the sensor may determine that the sensor is being worn on the clavicle and run a posture model for each person each time the person dons the exosuit.

After calibration and the appropriate posture model is identified, standard computations can be performed from the calibrated inertial measurement unit data to calculate a user's posture angle relative to a standard reference frame. In one embodiment, the exosuit system can performs this posture angle computation over twenty-five times per second (25 Hz). Other approaches may compute this angle computation on a more or less frequent basis—such as at 1 computation per second (1 Hz) or 100 times per second (100 Hz).

The posture angle data can be stored and analyzed for each sample, or averaged and stored over a number of samples. When averaged and stored over a number of samples, analytics and statistics can be computed and stored alongside the stored data to provide additional context in the compressed data. Data processing and storage can be performed over a fixed temporal window such as at every minute, five minute or ten minute intervals, or stored over an event driven window. Because posture angle data can be voluminous, some form of compression is generally required. System and methods for posture determination and data compression over a fixed time interval may be used, and in some variations may use approaches as described in U.S. Pat. No. 9,940,811 titled "SYSTEM AND METHOD OF BIOMECHANICAL POSTURE DETECTION AND FEEDBACK" and U.S. Pat. No. 9,936,900 titled "SYSTEM AND METHOD FOR BIOMECHANICAL POSTURE DETECTION AND FEEDBACK INCLUDING SENSOR NORMALIZATION" which are hereby incorporated herein in their entirety.

Posture data can be stored during specific activities such as standing and sitting. Posture data can also be stored for biking, horse riding, walking, running, sleeping, laying down, or any other activity. In cases where a user is sitting in a sedentary state, but fidgets in their chair, this motion can add significant motion artifacts that can change or cause the posture angle to fluctuate erratically and distort the data. One approach to addressing this noise is to average the data over the interval time and perform statistical analysis over that same time period. Another approach, referred to herein as posture session segmentation, is to ignore motion data over a specific threshold, and only analyze and make posture determinations during periods of low motion activity.

Posture sessions segmentation can identify, analyze, and store compressed relevant posture data over time. The temporal nature of posture data makes storing large continuous posture data inappropriate. Compressing data over uniformly sized fixed intervals is a solution to address the large storage problem, however it has its limitations for data mining and data analysis. Temporally, posture is extremely sparse with regions of little motion that are interrupted by quick and short movements. Since the distribution of these activities are not uniformly distributed, fixed-sampling does not abstract these fine details of general posture accurately. Identifying discrete time windows for posture analysis where there is low motion activity represents an approach to compressing posture data but increasing data quality for future cloud data mining analysis.

A difficulty in performing posture session segmentation is finding appropriate regions to segment the time-series that accurately reflects the sparse, natural behavior. Segmentation techniques that are too sensitive to motion will register any movement as a posture session and provide a poor compression, while segmentation techniques that are not sensitive enough to motion will incorporate too much data in a single session, leading to noisy data.

The ideal segmentation threshold segments the temporal data during times when a user makes shifts in their sedentary posture form such as a transition from good posture to bad posture, or when a user makes a transition from sitting straight to leaning backwards, forwards, left, and right. In addition to identifying a posture motion segmentation threshold, a filtered version of average user motion can be computed over a specific period of time.

A variety of different approaches can be used to segment posture sessions. For example, in one implementation, the time derivative of acceleration vector length, can be used to determine changes in movement. Other implementations can include comparing the magnitude of the acceleration vector, or its components, with pre-defined thresholds or adaptive thresholds trained on baseline user data. Additionally, these time varying signals may require some signal processing to emphasize the motion of interest and minimize the effects of sensor noise. In a preferred implementation, a combination of low-pass filters, band-pass filters, and logarithmic squared-error transfer functions were found to provide meaningful thresholds to segment posture sessions.

After posture segmentation is performed on the posture data, posture angles and statistics can be computed. Statistics such as standard deviation, mean, and confidence interval for each dimension can be computed and stored. This can help to characterize each posture session for deeper analysis in the future (e.g., cloud based analysis of the data). A posture session with low standard deviation and high confidence interval represents a user that had little motion or postural changes in a posture session, whereas a session with high standard deviation may represent a user who moved slowly during the posture session—slow enough that it did not segment the posture session. Consequently, posture sessions with large standard deviations and low confidence intervals can be weighted lower than sessions with low standard deviations and high confidence intervals.

Figure 5:
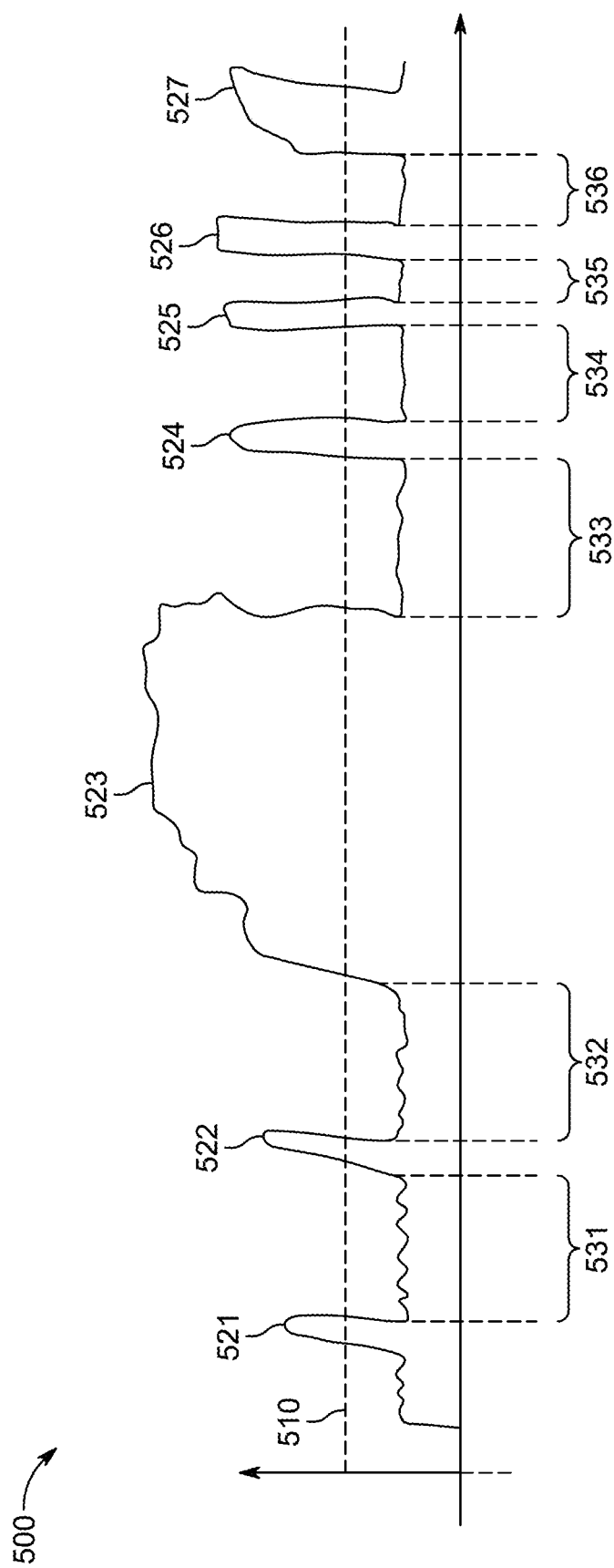
FIG. 5 shows an illustrative timing diagram 500 of movement data obtained from one or more sensors located on an exosuit according to an embodiment.

FIG. 5 shows an illustrative timing diagram 500 of movement data obtained from one or more sensors located on an exosuit according to an embodiment. Timing diagram 500 shows a magnitude of movement versus time. The time period represented in diagram 500 can represent a typical exosuit use period. For example, a typical exosuit use period may be 8-24 hours, a week, a month, or a year. The movement data can be classified as relatively high user activity or relatively low user activity. Activity threshold 510 may define a threshold that determines whether the data is associated with relatively high user activity or relatively low user activity. As shown, several relatively high user activity segments are shown as segments 521-527. For example, segment 523 can represent a time when an exosuit user is walking around and segments 521, 522, and 524-527 can represent times when the exosuit user is fidgeting in a seated position, or getting up or sitting down. In addition, several relatively low user activity segments are shown as segments 531-536. Segments 531-536 can times when the exosuit is sitting relatively still (without fidgeting) or standing (without fidgeting). Relatively low user activity segments 531-536 typically exist between relatively high user activity segments. For purposes of posture segmentation analysis, the relatively high user activity segments can be discarded or ignored, and the relatively low user activity segments can be identified and further analyzed in accordance with posture session segment analysis according to embodiments discussed herein. Ignoring the relatively high user activity segments can assist the posture segment analysis in focusing on data that is more pertinent to posture analysis during events of low activity, thereby saving on storage space that would otherwise be required to store data for both high and low activity segments.

After the posture segments (e.g., segments 531-536) are identified, the posture session data from each segment is analyzed. The posture analysis can specify forward/backward lean angle of the user and left/right lean angle of the user. These lean angles can be used to indicate whether the person has a forward slouch, a backward slouch, a forward slouch with a moderate left lean, etc.

Figure 6A:
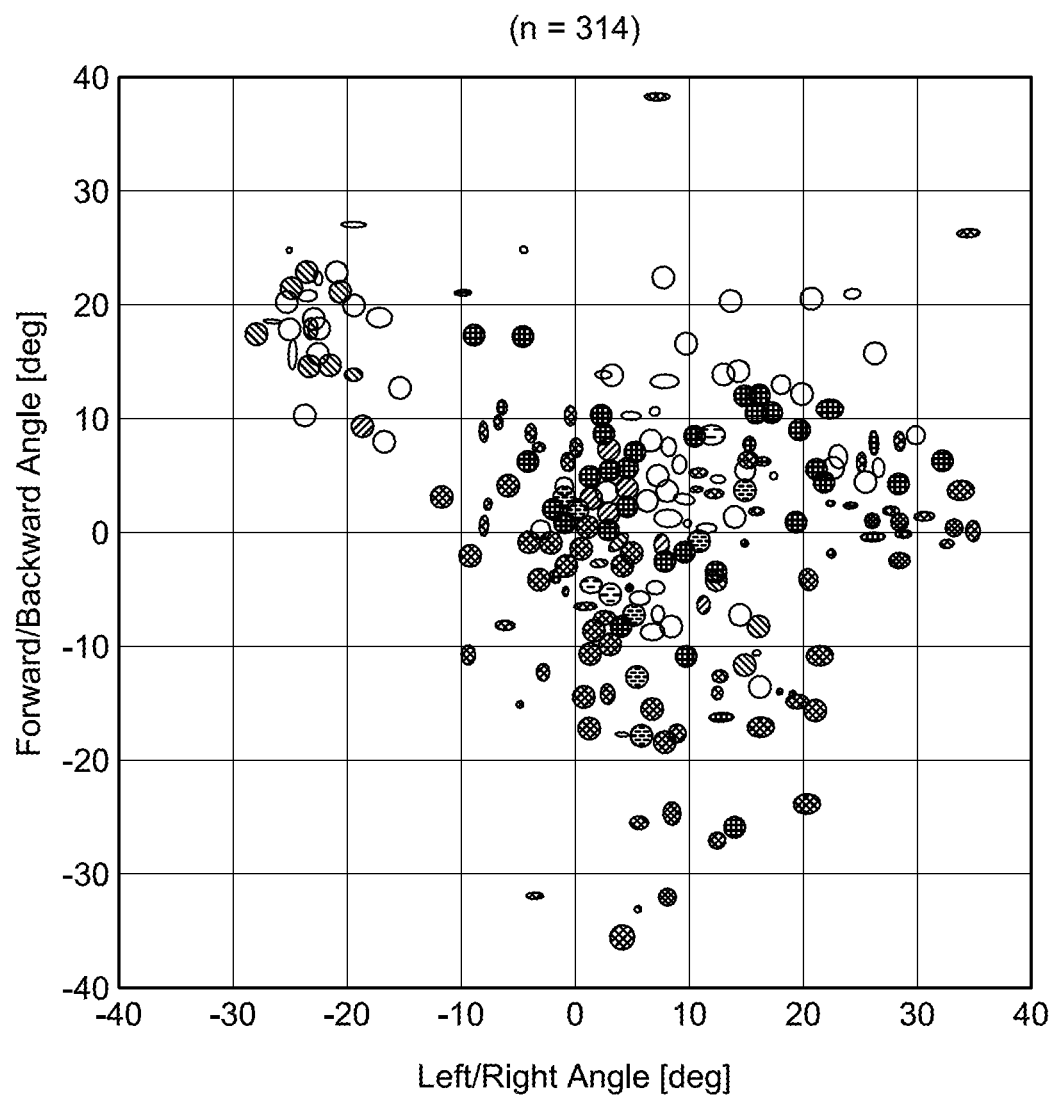
FIGS. 6A-6C show illustrative graphs showing posture information according to various embodiments.
Figure 6B:
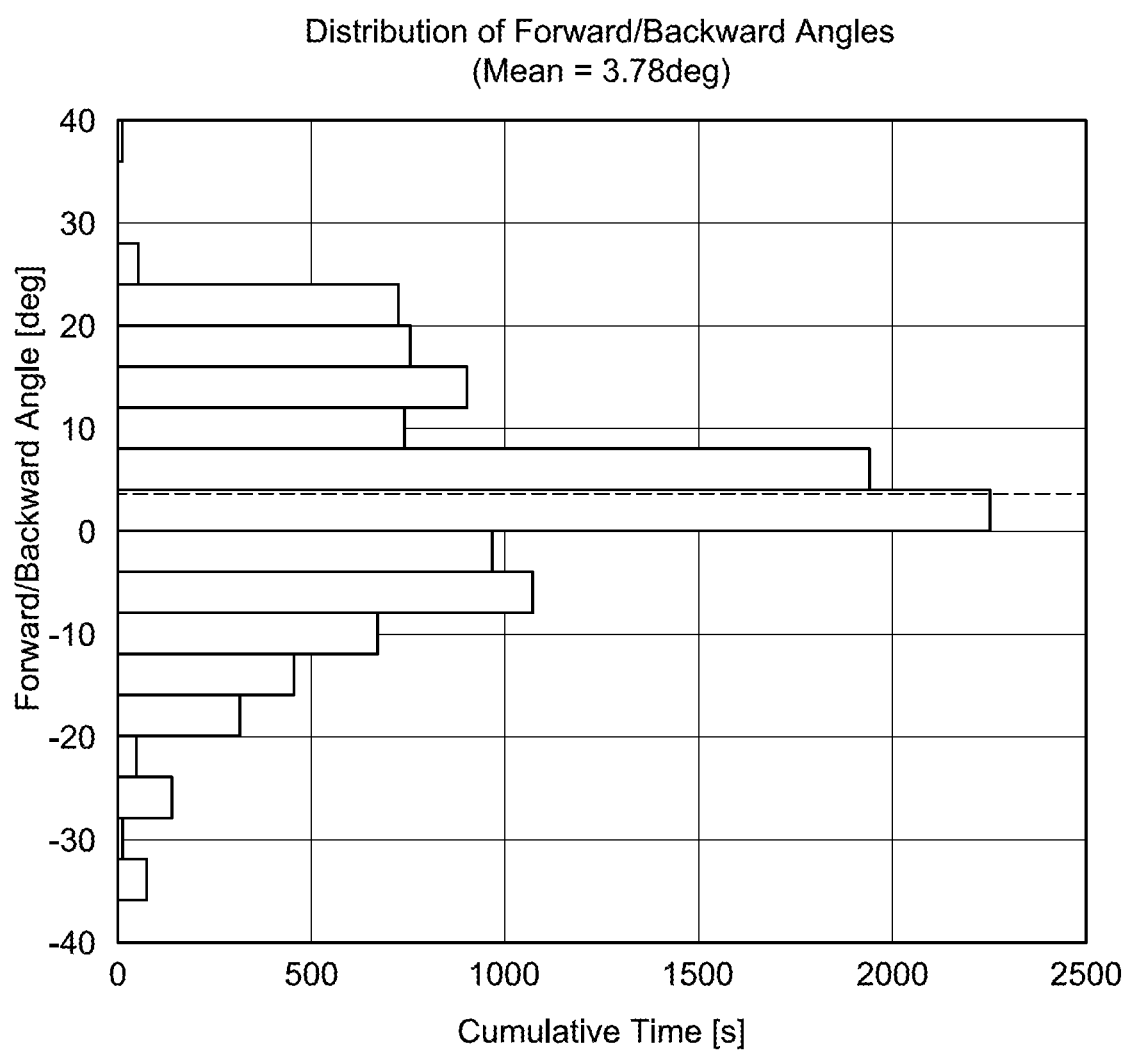
Figure 6C:
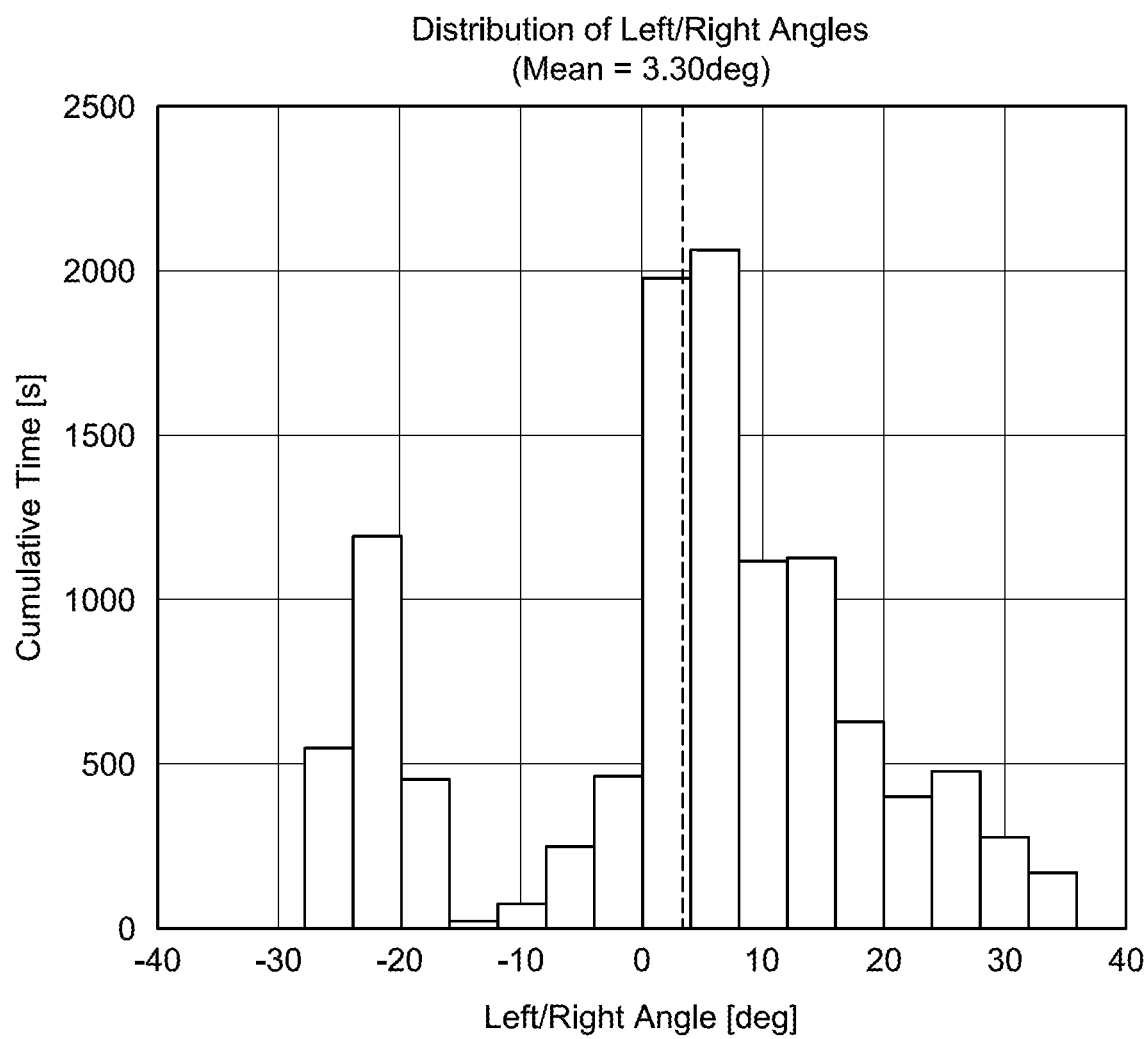

FIGS. 6A-6C show illustrative graphs showing posture information according to various embodiments. FIG. 6A shows posture session data for 314 posture sessions pertaining to a person when viewed from above the person. In particular, FIG. 6A shows position of the person on the transverse plane. Each dot in FIG. 6A represents a posture position along the forward/backward angle and the left/right angle. In some embodiments, the dots can be color coded to correspond with a particular time frame with thing the exosuit use period. For example, the exosuit use period can be segmented into five time frames and the dots can correspond to one of these five time frames. This way, when the dots are plotted in the graph, one can see how posture changes throughout the exosuit use period. FIG. 6B shows how long the user has spent at different ranges of forward/backward angles and FIG. 6C shows how long the user has spent at different ranges of left/right angles. The posture session data can be weighted by time duration, standard deviation, confidence interval or any other characteristic. If desired, the posture session data can be graphed every hour, day, week or over any specific period of time.

It has been observed that posture behavior can change throughout the day. This may depend on a multitude of factors. For example, the user may be full of energy during in the early part of the day, but may grow tired by the end of the day, and as result, the user's posture may change. Therefore, a user may have a particular posture classification such as a forward lean, and may shift to a backward lean toward the end of the day. Classifying posture behaviors allow the coaching program to adjust throughout the day providing feedback, exercises and tips to adjust for forward lean, and then another set of feedback, exercises and tips for adjusting to backward lean during the end of the day. The postures session analysis can observe these changes and provide exosuit feedback to compensate for changes in daily posture positions, or provide some other feedback to assist the user.

Posture segment data can be analyzed together with activity data to provide more context. For example, posture positional data with context of significant sedentary time can be treated differently from posture positional data with very little sedentary time. In one example, strong posture feedback (such as auditory or vibrational feedback reminders or exosuit enabled assistance) can be provided to the user with poor posture data and long sedentary time, while the posture feedback may not be triggered in scenarios where the user exhibits poor posture data, but for low sedentary period of time. In another example, posture feedback for a user with poor posture data and long sedentary time can be provided to the user with a message such as "get up and walk around" whereas a user with poor posture data and low sedentary time can be provided a simple vibratory buzz or auditory feedback to "get back into good posture".

In another example, if the user exhibits poor posture, rather than just vibratory feedback interventions, the exosuit can provide direct intervention by providing assistive support to the user based on the posture segment analysis. For example, the exosuit can provide assistive support around the thoracic and lumbar spine regions of the user based on the longitudinal data obtained from the posture segment analysis. In some embodiments, the posture segment data can be used to provide reactive corrective assistance (e.g., relatively instantaneous posture segment data can cause the exosuit to activate the appropriate power layers to compensate for poor posture). In other embodiments, when posture segment data has been accumulated over a period time and patterns are recognized in user posture, the exosuit can provide pre-emptive corrective assistance. For example, if the pattern indicates that the user exhibits poor posture in the afternoon, but not in the morning, the exosuit can provide pre-emptive correction assistance in the afternoon to counteract the expected poor posture in the afternoon.

In addition, unsupervised learning clustering algorithms can be used to find other patterns in the posture data. These approaches include k-means, expectation-maximization algorithms, density-based clustering, principal component analysis, and auto-encoding deep learning networks to identify different posture behaviors or position-clusters, which would correspond to a particular behavior. By using an unsupervised learning algorithm, the model can find natural boundaries between the types of posture positions, time of day, activity data, feedback events, location, demographic, weather and any other relevant dataset.

Various types of feedback can be provided to a user in real-time, daily, weekly or monthly intervals. For example, a user could have a weekly phone call with a posture coach or get a weekly email on progress and suggested exercises or things to focus on for the following week. Snapshots of the posture information graphs can be analyzed along with feedback types to determine which feedback mechanisms work the best in shifting a user from one posture position to another. Feedback can be analyzed to determine when and which types of feedback is most effective in shifting a user from a poor posture position to a better posture position.

In addition, pre/post posture session data can be used to evaluate the effectiveness of various feedback interventions and intervention parameters for each individual. Every user may respond differently and these differences may change overtime. For example, pre/post posture session data can be used to evaluate the effectiveness of real-time vibratory feedback (or exosuit enforced posture re-alignment) when a user is in bad posture for too long. After a vibration feedback event or exosuit correction event, the system can analyze the posture session data before and after the event to determine if a user changed their posture behavior. Parameters of the vibrational feedback and exosuit correction can be varied and tested for how well a user reacts to the feedback. Some parameters may include bad posture delay timer (ie. allowing a user to slouch for 10 seconds before getting the posture feedback), bad posture threshold (ie. the posture position determined as bad posture relative to the posture position determined as good posture), vibration intensity, vibration pattern, number of vibrations or vibration feedback attempts if a user is still in bad posture.

Figure 7A:
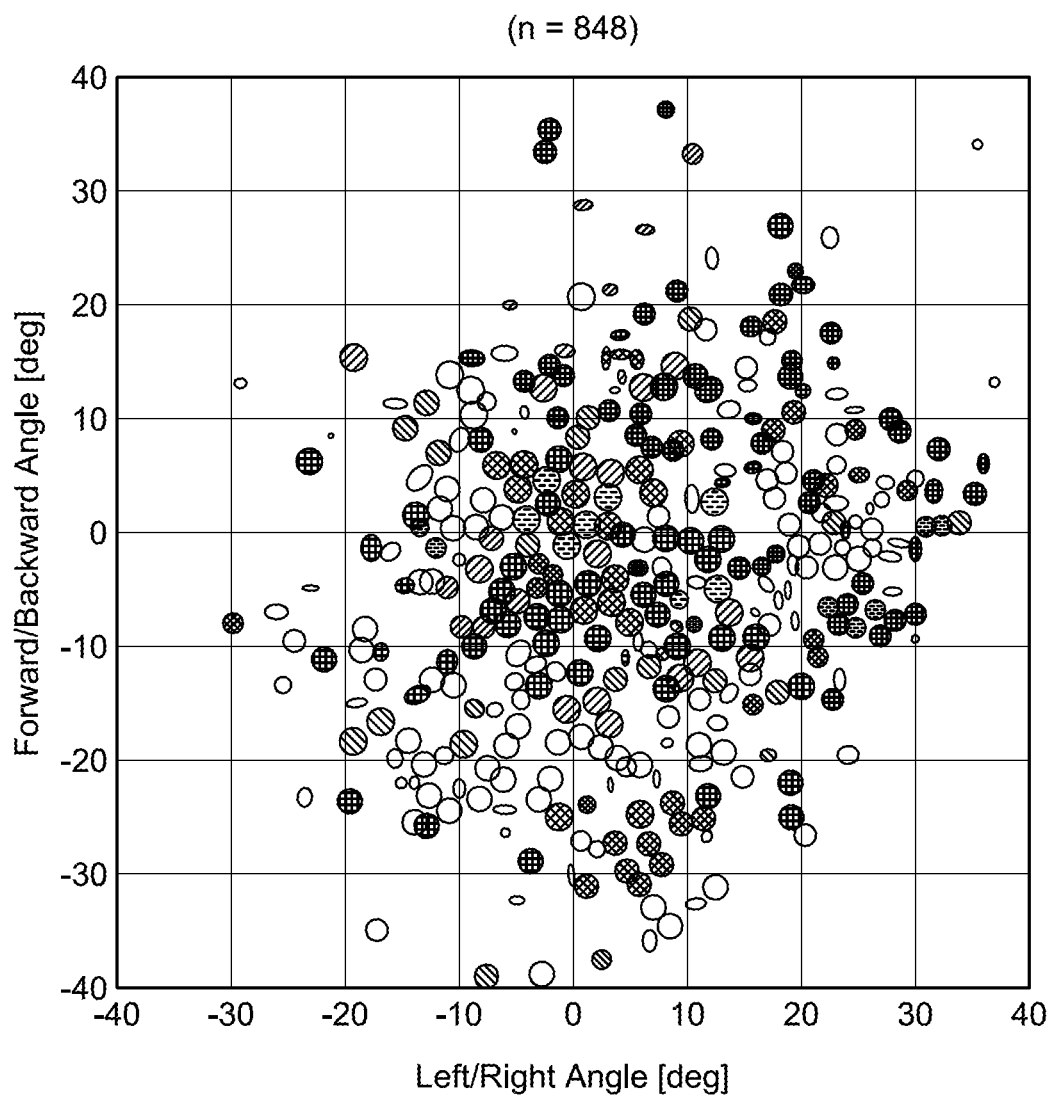
FIGS. 7A and 7B show illustrative posture data without posture feedback and with posture feedback, respectively, according to an embodiment.
Figure 7B:
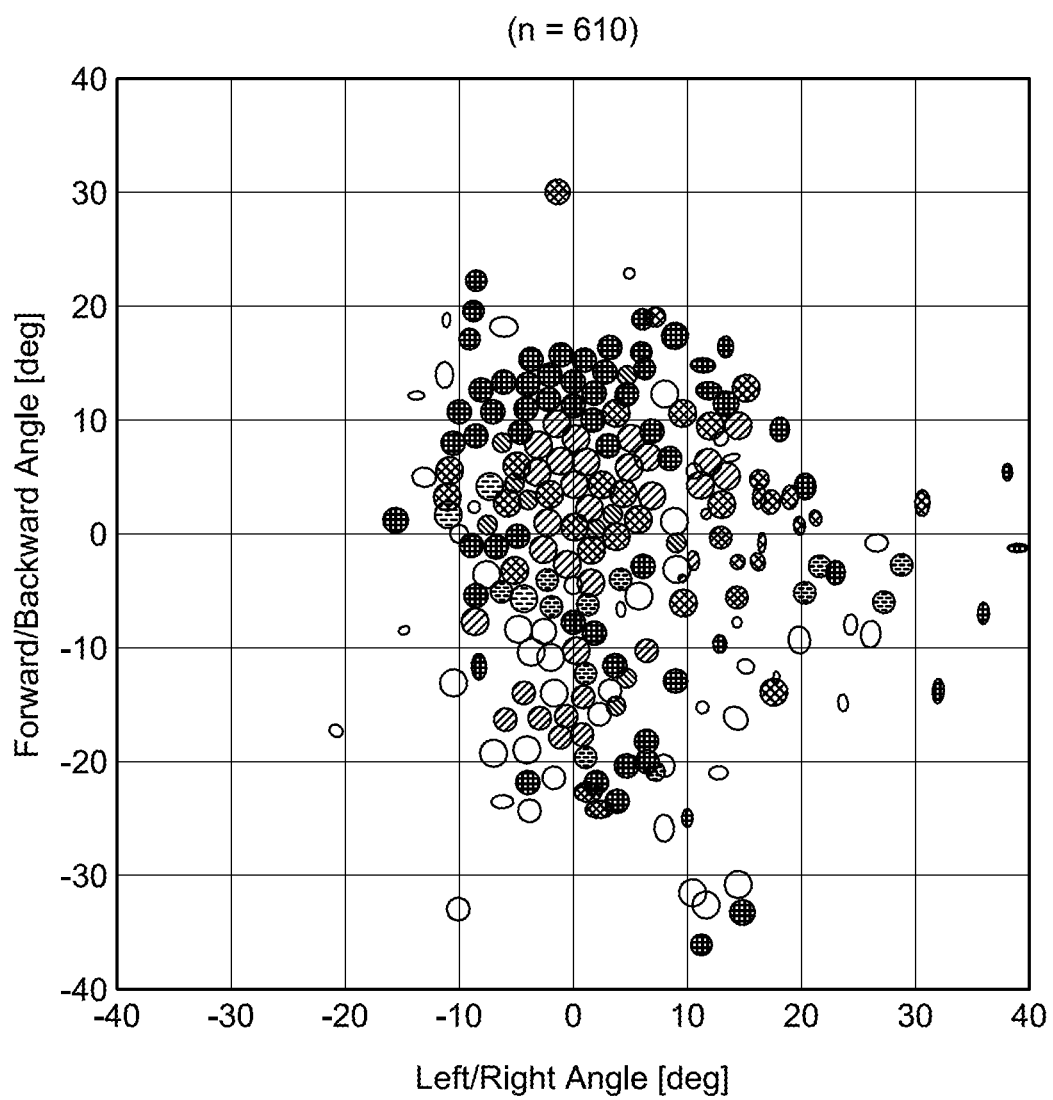

FIGS. 7A and 7B show illustrative posture data without posture feedback and with posture vibrational feedback, respectively, according to an embodiment. Notice how the plots in FIG. 7A are more spread apart and the data in FIG. 7B are more concentrated (e.g., around a good posture zone). The good posture zone can include forward/back angles and left/right angles near zero, or between zero and one degree, between zero and five degrees. The concentration of data point within the good posture zone may be due to posture feedback.

Posture segment data can be accumulated from all or a subset of exosuit users. If desired, studies can be conducted to run randomized control studies to identify the types of feedback and their characteristics that can help improve particular groups of people improve their posture or activity levels. For example, groups of people could be determined by demographic data or posture position behavior (ie forward slouchers, backward slouches, left leaning slouchers, after-lunch slouchers, meeting slouchers, etc). Posture feedback programs can be personalized based on multiple factors.

In some embodiments, pain data can be correlated with posture position data to understand how each individual responds to their pain. The pain data can be supplied by the user, for example, by requiring the user to indicate that they are currently experiencing pain or when they were experiencing pain. Pain data can be captured by the application with multiple approaches. During the onboarding process, a user can elect to disclose whether or not they have pain, pain severity, length of time they've had pain, pain location, and other characteristics of the pain. A pain survey, such as from 0-10, can be used to quantify pain with a particular frequency and timeframe. For example, a pain data survey can be prompted to the user everyday, or every other day. This survey could also be embedded into a user's daily report which could include posture data and activity data where a user can track how they feel with how well they had good posture and how active they were. The pain and posture position data could be used to provide even further personalized coaching for an individual user. For example, if a user has lower back pain and is leaning backwards to cope with the back pain, the coaching program may avoid providing feedback to straighten up and instead provide feedback to ensure proper back support such as a cushion or backrest is used to help stabilize the lower back. Exercises to help improve low back mobility may also be recommended, such as a lower back stretch, cat stretch, or child's pose. Longitudinal changes in pain data and posture data behavior can be used to understand feedback effectiveness.

In another instance, if a user has lower back pain and is leaning backwards to cope with the back pain, an exosuit can provide more specific support by using LDMs and power layers to strengthen the body and restrict movement around the lumbar sections, while providing less support and more freedom in the thoracic sections. In another instance, if a user has upper back pain, the exosuit can provide more specific support by using LDMs and power layers to strengthen the body and restrict movement around the thoracic sections, while providing less support and more freedom in the lumbar sections.

Figure 8A:
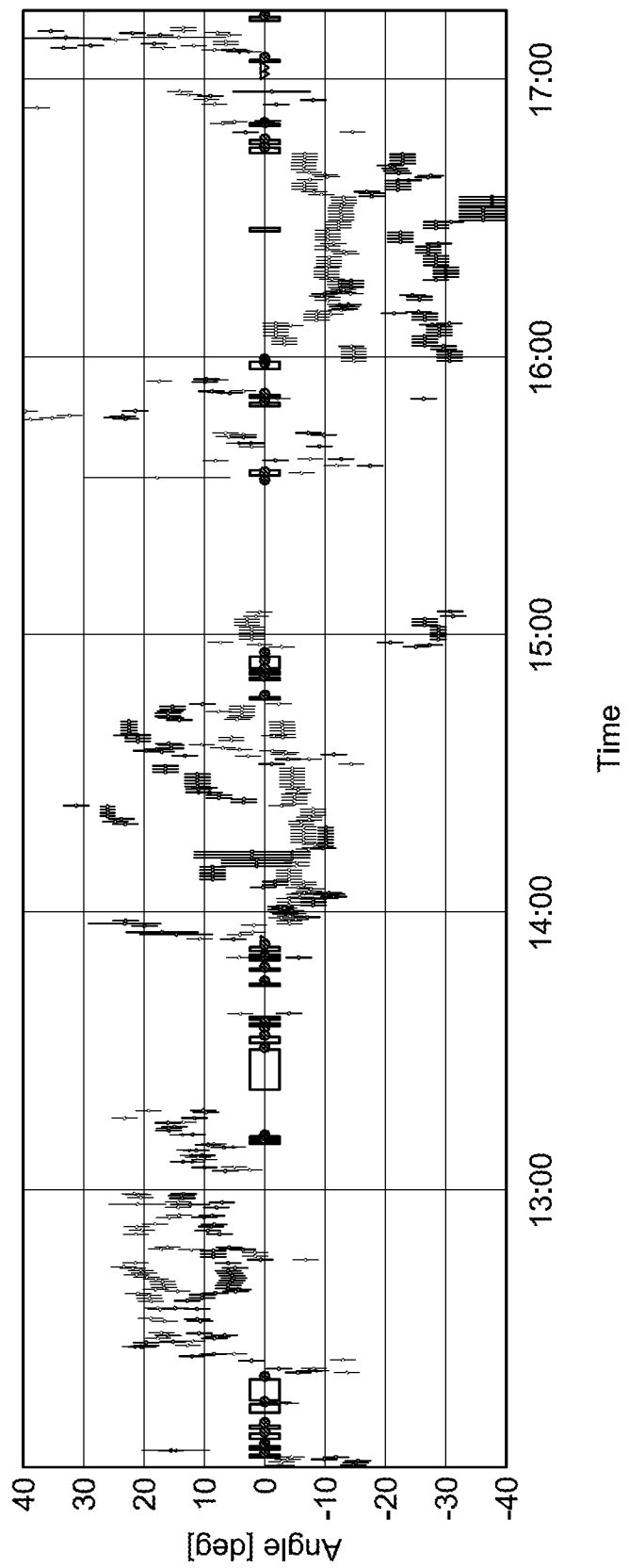
FIGS. 8A and 8B show illustrative before and after posture plots according to an embodiment.
Figure 8B:
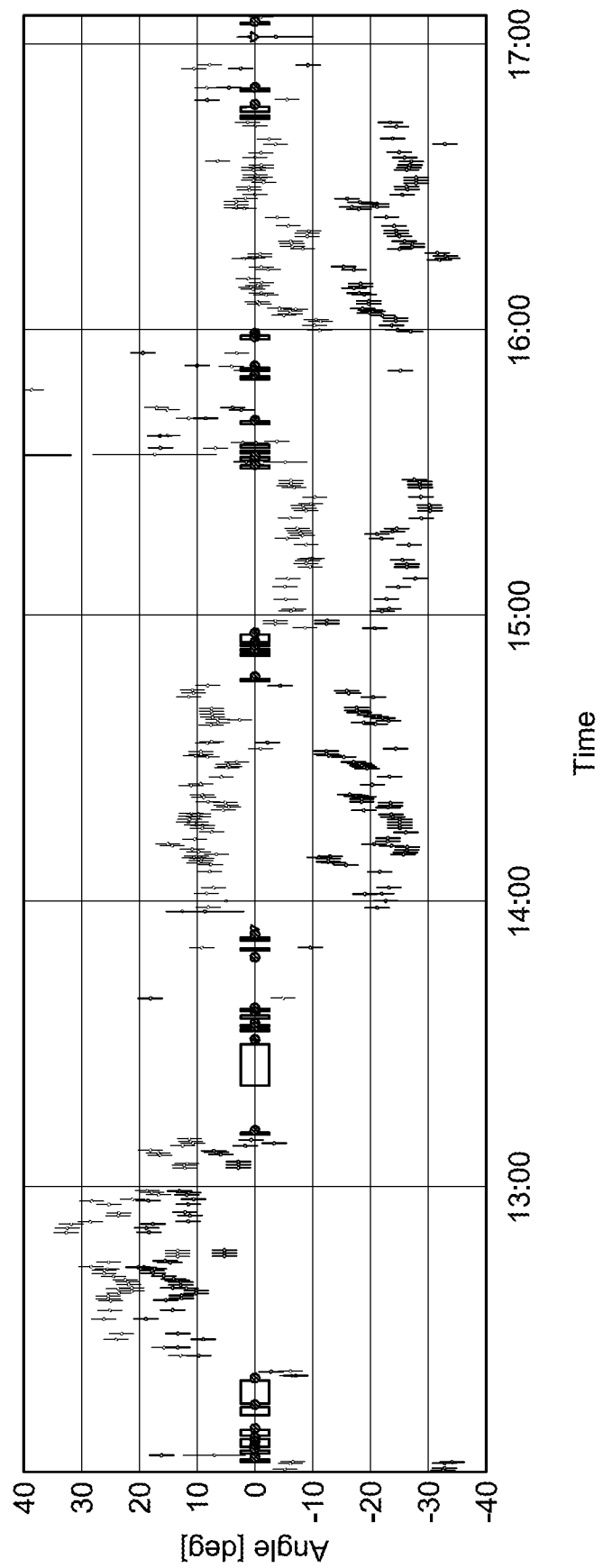

In addition to detecting posture sessions for analyzing posture data, large changes in standard deviation may be an indicator for the instability of a portion of the exosuit as it is fitted to the user. In one example, if the exosuit is not property fit or secured to the user, and the user does not move, but one or more sensors still shift in angle, thereby creating a large deviation in angle change within a single posture session, instability resulting from the exosuit can be detected. This pattern is apparent in FIGS. 8A and 8B during the periods from 2-3 pm and 4-5 pm. Notice how the standard deviation of the forward/backward angle is significantly larger in FIG. 8A compared to the forward/backward standard deviation in FIG. 8B during the same period of time. The standard deviation of the angle is indicated by the confidence interval bands. Data from FIG. 8A came from a sensor worn on a loose garment, and data from FIG. 8B came from a separate sensor adhered to a user's skin. Both sensors were worn at the same time on the same user. It is also interesting to note that in FIG. 8A, the standard deviation values were significantly higher in the afternoon compared to in the morning.

Detecting loose clothing or sensor instability is a proactive approach to letting the user know that their exosuit is not stable and that the posture computations may be susceptible to more noise due to additional motion artifacts. If an unstable sensor is determined, the application can proactively tell a user to manually calibrate, or may tell the user to get into good posture for a few seconds and start the manual calibration sequence automatically.

Figure 9:
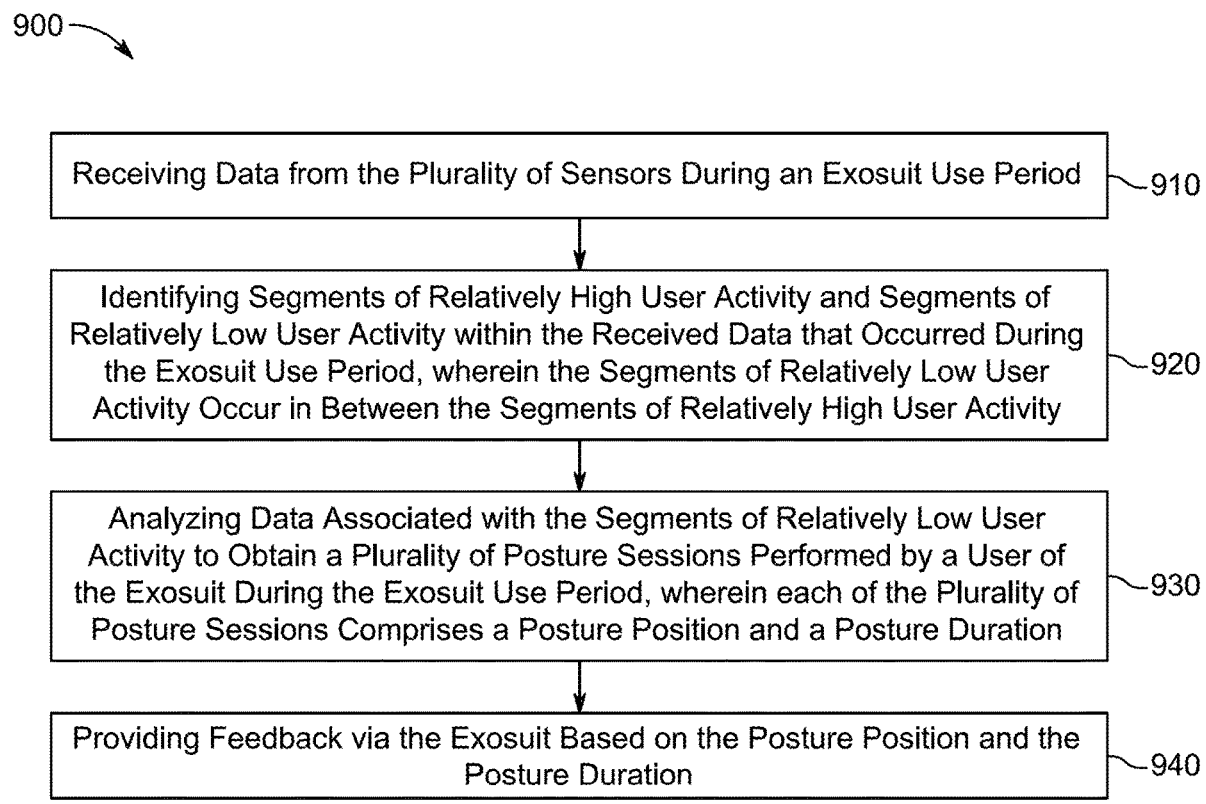
FIG. 9 shows illustrative process 900 according to an embodiment.

FIG. 9 shows illustrative process 900 according to an embodiment. The process can be implemented in an exosuit that includes a base layer, a power layer, and one or more sensors. Starting at step 910, data is received from the plurality of sensors during an exosuit use period. At step 920, segments of relatively high user activity and segments of relatively low user activity are identified within the received data that occurred during the exosuit use period, wherein the segments of relatively low user activity occur in between the segments of relatively high user activity. At step 930, data associated with the segments of relatively low user activity can be analyzed to obtain a plurality of posture sessions performed by a user of the exosuit during the exosuit use period. Each of the plurality of posture sessions can include a posture position and a posture duration. The posture position can a forward/backward lean angle and a left/right lean angle.

At step 940, feedback can be provided via the exosuit based on the posture position and the posture duration. In one embodiment, when the posture position for one of the posture sessions is classified as a relatively poor posture position and the posture duration exceeds a first time threshold, feedback is provided via the exosuit. The feedback can include exosuit assistance motion, an audio cue, or a haptic cue. In another embodiment, when the posture position for one of the posture sessions is classified as a relatively poor posture position and the posture duration is less than a second time threshold, the feedback can be prevented.

In yet other embodiments, the posture sessions can be clustered according to the posture position and a time of day. In yet another embodiment, the data associated with the segments of relatively high user activity can be discarded and the data associated with each posture session can be compressed. If desired, the compressed data can be uploaded to a server via a wireless or wired connection.

In other embodiments, the posture segmentation algorithm can verify that the feedback is improving posture. In addition, the posture segmentation algorithm can detect an improper fit of a portion of the exosuit exists based on the posture sessions and can provide notice to the user of the exosuit of the improper fit.

It should be appreciated that the steps shown in FIG. 9 are merely illustrative and that additional steps may be added.

Figure 10:
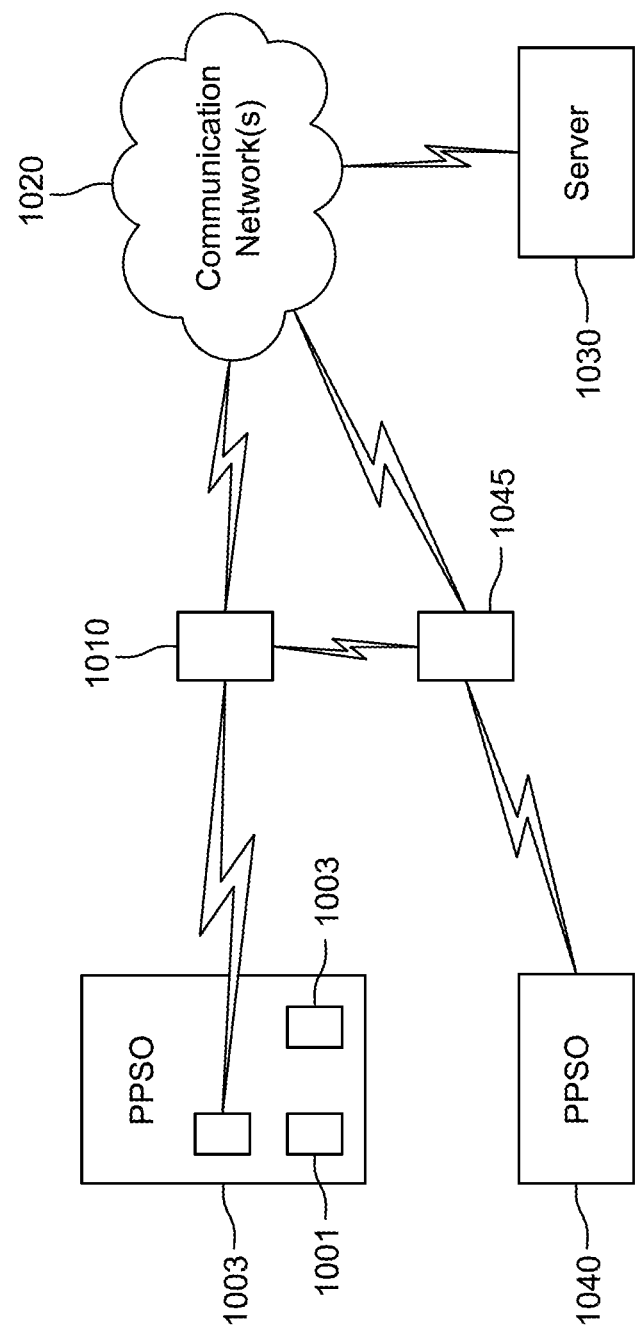
FIG. 10 illustrates an example exosuit according to an embodiment.

FIG. 10 illustrates an example exosuit 1000 that includes actuators 1001, sensors 1003, and a controller configured to operate elements of exosuit 1000 (e.g., 1001, 1003) to enable functions of the exosuit 1000. The controller 1005 is configured to communicate wirelessly with a user interface 1010. The user interface 1010 is configured to present information to a user (e.g., a wearer of the exosuit 1000) and to the controller 1005 of the flexible exosuit or to other systems. The user interface 1010 can be involved in controlling and/or accessing information from elements of the exosuit 1000. For example, an application being executed by the user interface 1010 can access data from the sensors 1003, calculate an operation (e.g., to apply dorsiflexion stretch) of the actuators 1001, and transmit the calculated operation to the exosuit 1000. The user interface 1010 can additionally be configured to enable other functions; for example, the user interface 1010 can be configured to be used as a cellular telephone, a portable computer, an entertainment device, or to operate according to other applications.

The user interface 1010 can be configured to be removably mounted to the exosuit 1000 (e.g., by straps, magnets, Velcro, charging and/or data cables). Alternatively, the user interface 1010 can be configured as a part of the exosuit 1000 and not to be removed during normal operation. In some examples, a user interface can be incorporated as part of the exosuit 1000 (e.g., a touchscreen integrated into a sleeve of the exosuit 1000) and can be used to control and/or access information about the exosuit 1000 in addition to using the user interface 1010 to control and/or access information about the exosuit 1000. In some examples, the controller 1005 or other elements of the exosuit 1000 are configured to enable wireless or wired communication according to a standard protocol (e.g., Bluetooth, ZigBee, WiFi, LTE or other cellular standards, IRdA, Ethernet) such that a variety of systems and devices can be made to operate as the user interface 1010 when configured with complementary communications elements and computer-readable programs to enable such functionality.

The exosuit 1000 can be configured as described in example embodiments herein or in other ways according to an application. The exosuit 1000 can be operated to enable a variety of applications. The exosuit 1000 can be operated to enhance the strength of a wearer by detecting motions of the wearer (e.g., using sensors 1003) and responsively applying torques and/or forces to the body of the wearer (e.g., using actuators 1001) to increase the forces the wearer is able to apply to his/her body and/or environment. The exosuit 1000 can be operated to train a wearer to perform certain physical activities. For example, the exosuit 1000 can be operated to enable rehabilitative therapy of a wearer. The exosuit 1000 can operate to amplify motions and/or forces produced by a wearer undergoing therapy in order to enable the wearer to successfully complete a program of rehabilitative therapy. Additionally or alternatively, the exosuit 1000 can be operated to prohibit disordered movements of the wearer and/or to use the actuators 1001 and/or other elements (e.g., haptic feedback elements) to indicate to the wearer a motion or action to perform and/or motions or actions that should not be performed or that should be terminated. Similarly, other programs of physical training (e.g., dancing, skating, other athletic activities, vocational training) can be enabled by operation of the exosuit 1000 to detect motions, torques, or forces generated by a wearer and/or to apply forces, torques, or other haptic feedback to the wearer. Other applications of the exosuit 100 and/or user interface 1010 are anticipated.

The user interface 1010 can additionally communicate with communications network(s) 1020. For example, the user interface 1010 can include a WiFi radio, an LTE transceiver or other cellular communications equipment, a wired modem, or some other elements to enable the user interface 1010 and exosuit 1000 to communicate with the Internet. The user interface 1010 can communicate through the communications network 1020 with a server 1030. Communication with the server 1030 can enable functions of the user interface 1010 and exosuit 1000. In some examples, the user interface 1010 can upload telemetry data (e.g., location, configuration of elements 1001, 1003 of the exosuit 1000, physiological data about a wearer of the exosuit 1000) to the server 1030.

In some examples, the server 1030 can be configured to control and/or access information from elements of the exosuit 1000 (e.g., 1001, 1003) to enable some application of the exosuit 1000. For example, the server 1030 can operate elements of the exosuit 1000 to move a wearer out of a dangerous situation if the wearer was injured, unconscious, or otherwise unable to move themselves and/or operate the exosuit 1000 and user interface 1010 to move themselves out of the dangerous situation. Other applications of a server in communications with a exosuit are anticipated.

The user interface 1010 can be configured to communicate with a second user interface 1045 in communication with and configured to operate a second flexible exosuit 1040. Such communication can be direct (e.g., using radio transceivers or other elements to transmit and receive information over a direct wireless or wired link between the user interface 1010 and the second user interface 1045). Additionally or alternatively, communication between the user interface 1010 and the second user interface 1045 can be facilitated by communications network(s) 1020 and/or a server 1030 configured to communicate with the user interface 1010 and the second user interface 1045 through the communications network(s) 1020.

Communication between the user interface 1010 and the second user interface 1045 can enable applications of the exosuit 1000 and second exosuit 1040. In some examples, actions of the exosuit 1000 and second flexible exosuit 1040 and/or of wearers of the exosuit 1000 and second exosuit 1040 can be coordinated. For example, the exosuit 1000 and second exosuit 1040 can be operated to coordinate the lifting of a heavy object by the wearers. The timing of the lift, and the degree of support provided by each of the wearers and/or the exosuit 1000 and second exosuit 1040 can be controlled to increase the stability with which the heavy object was carried, to reduce the risk of injury of the wearers, or according to some other consideration. Coordination of actions of the exosuit 1000 and second exosuit 1040 and/or of wearers thereof can include applying coordinated (in time, amplitude, or other properties) forces and/or torques to the wearers and/or elements of the environment of the wearers and/or applying haptic feedback (though actuators of the exosuits 1000, 1040, through dedicated haptic feedback elements, or through other methods) to the wearers to guide the wearers toward acting in a coordinated manner.

Coordinated operation of the exosuit 1000 and second exosuit 1040 can be implemented in a variety of ways. In some examples, one exosuit (and the wearer thereof) can act as a master, providing commands or other information to the other exosuit such that operations of the exosuit 1000, 1040 are coordinated. For example, the exosuit 1000, 1040 can be operated to enable the wearers to dance (or to engage in some other athletic activity) in a coordinated manner. One of the exosuits can act as the 'lead', transmitting timing or other information about the actions performed by the 'lead' wearer to the other exosuit, enabling coordinated dancing motions to be executed by the other wearer. In some examples, a first wearer of a first exosuit can act as a trainer, modeling motions or other physical activities that a second wearer of a second exosuit can learn to perform. The first exosuit can detect motions, torques, forces, or other physical activities executed by the first wearer and can send information related to the detected activities to the second exosuit. The second exosuit can then apply forces, torques, haptic feedback, or other information to the body of the second wearer to enable the second wearer to learn the motions or other physical activities modeled by the first wearer. In some examples, the server 1030 can send commands or other information to the exosuits 1000, 1040 to enable coordinated operation of the exosuits 1000, 1040.

The exosuit 1000 can be operated to transmit and/or record information about the actions of a wearer, the environment of the wearer, or other information about a wearer of the exosuit 1000. In some examples, kinematics related to motions and actions of the wearer can be recorded and/or sent to the server 1030. These data can be collected for medical, scientific, entertainment, social media, or other applications. The data can be used to operate a system. For example, the exosuit 1000 can be configured to transmit motions, forces, and/or torques generated by a user to a robotic system (e.g., a robotic arm, leg, torso, humanoid body, or some other robotic system) and the robotic system can be configured to mimic the activity of the wearer and/or to map the activity of the wearer into motions, forces, or torques of elements of the robotic system. In another example, the data can be used to operate a virtual avatar of the wearer, such that the motions of the avatar mirrored or were somehow related to the motions of the wearer. The virtual avatar can be instantiated in a virtual environment, presented to an individual or system with which the wearer is communicating, or configured and operated according to some other application.

Conversely, the exosuit 1000 can be operated to present haptic or other data to the wearer. In some examples, the actuators 1001 (e.g., twisted string actuators, exotendons) and/or haptic feedback elements (e.g., EPAM haptic elements) can be operated to apply and/or modulate forces applied to the body of the wearer to indicate mechanical or other information to the wearer. For example, the activation in a certain pattern of a haptic element of the exosuit 1000 disposed in a certain location of the exosuit 1000 can indicate that the wearer had received a call, email, or other communications. In another example, a robotic system can be operated using motions, forces, and/or torques generated by the wearer and transmitted to the robotic system by the exosuit 1000. Forces, moments, and other aspects of the environment and operation of the robotic system can be transmitted to the exosuit 1000 and presented (using actuators 10801 or other haptic feedback elements) to the wearer to enable the wearer to experience force-feedback or other haptic sensations related to the wearer's operation of the robotic system. In another example, haptic data presented to a wearer can be generated by a virtual environment, e.g., an environment containing an avatar of the wearer that is being operated based on motions or other data related to the wearer that is being detected by the exosuit 1000.

Note that the exosuit 1000 illustrated in FIG. 10 is only one example of a exosuit that can be operated by control electronics, software, or algorithms described herein. Control electronics, software, or algorithms as described herein can be configured to control flexible exosuits or other mechatronic and/or robotic system having more, fewer, or different actuators, sensors or other elements. Further, control electronics, software, or algorithms as described herein can be configured to control exosuits configured similarly to or differently from the illustrated exosuit 1000. Further, control electronics, software, or algorithms as described herein can be configured to control flexible exosuits having reconfigurable hardware (i.e., exosuits that are able to have actuators, sensors, or other elements added or removed) and/or to detect a current hardware configuration of the flexible exosuits using a variety of methods.

A controller of a exosuit and/or computer-readable programs executed by the controller can be configured to provide encapsulation of functions and/or components of the flexible exosuit. That is, some elements of the controller (e.g., subroutines, drivers, services, daemons, functions) can be configured to operate specific elements of the exosuit (e.g., a twisted string actuator, a haptic feedback element) and to allow other elements of the controller (e.g., other programs) to operate the specific elements and/or to provide abstracted access to the specific elements (e.g., to translate a command to orient an actuator in a commanded direction into a set of commands sufficient to orient the actuator in the commanded direction). This encapsulation can allow a variety of services, drivers, daemons, or other computer-readable programs to be developed for a variety of applications of a flexible exosuits. Further, by providing encapsulation of functions of a flexible exosuit in a generic, accessible manner (e.g., by specifying and implementing an application programming interface (API) or other interface standard), computer-readable programs can be created to interface with the generic, encapsulated functions such that the computer-readable programs can enable operating modes or functions for a variety of differently-configured exosuit, rather than for a single type or model of flexible exosuit. For example, a virtual avatar communications program can access information about the posture of a wearer of a flexible exosuit by accessing a standard exosuit API. Differently-configured exosuits can include different sensors, actuators, and other elements, but can provide posture information in the same format according to the API. Other functions and features of a flexible exosuit, or other robotic, exoskeletal, assistive, haptic, or other mechatronic system, can be encapsulated by APIs or according to some other standardized computer access and control interface scheme.

Figure 11:
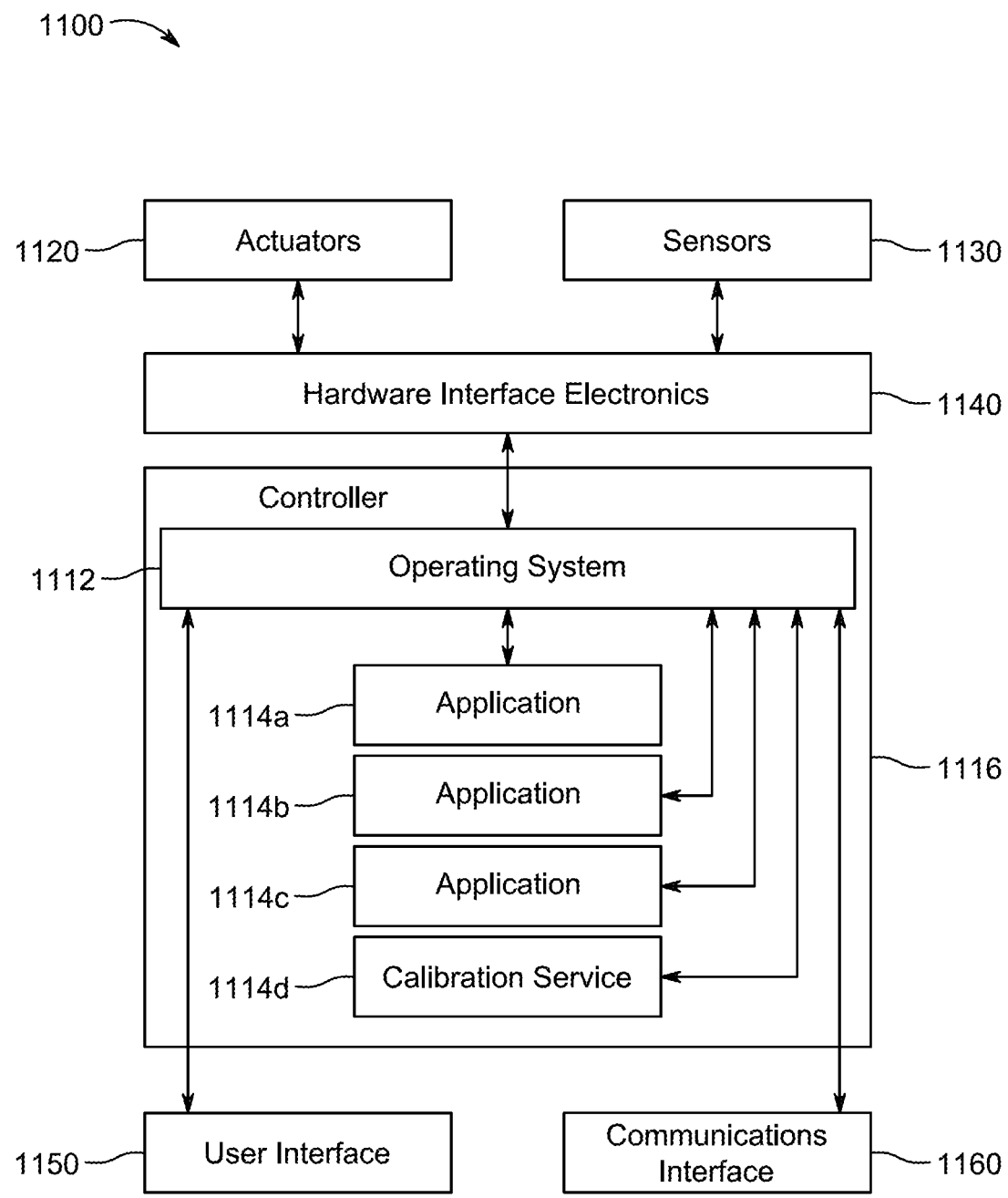
FIG. 11 is a schematic illustrating elements of an exosuit and a hierarchy of control or operating the exosuit according to an embodiment.

FIG. 11 is a schematic illustrating elements of a exosuit 1100 and a hierarchy of control or operating the exosuit 1100. The flexible exosuit includes actuators 1120 and sensors 1130 configured to apply forces and/or torques to and detect one or more properties of, respectively, the exosuit 1100, a wearer of the exosuit 1100, and/or the environment of the wearer. The exosuit 1100 additionally includes a controller 1110 configured to operate the actuators 1120 and sensors 1130 by using hardware interface electronics 1140. The hardware electronics interface 1140 includes electronics configured to interface signals from and to the controller 1110 with signals used to operate the actuators 1120 and sensors 1130. For example, the actuators 1120 can include exotendons, and the hardware interface electronics 1140 can include high-voltage generators, high-voltage switches, and high-voltage capacitance meters to clutch and un-clutch the exotendons and to report the length of the exotendons. The hardware interface electronics 1140 can include voltage regulators, high voltage generators, amplifiers, current detectors, encoders, magnetometers, switches, controlled-current sources, DACs, ADCs, feedback controllers, brushless motor controllers, or other electronic and mechatronic elements.

The controller 1110 additionally operates a user interface 1150 that is configured to present information to a user and/or wearer of the exosuit 1100 and a communications interface 1960 that is configured to facilitate the transfer of information between the controller 1110 and some other system (e.g., by transmitting a wireless signal). Additionally or alternatively, the user interface 1150 can be part of a separate system that is configured to transmit and receive user interface information to/from the controller 1110 using the communications interface 1960 (e.g., the user interface 1150 can be part of a cellphone).

The controller 1110 is configured to execute computer-readable programs describing functions of the flexible exosuit 1112. Among the computer-readable programs executed by the controller 1110 are an operating system 1112, applications 1114*a*, 1114*b*, 1114*c*, and a calibration service 1116. The operating system 1112 manages hardware resources of the controller 1110 (e.g., I/O ports, registers, timers, interrupts, peripherals, memory management units, serial and/or parallel communications units) and, by extension, manages the hardware resources of the exosuit 1100. The operating system 1112 is the only computer-readable program executed by the controller 1110 that has direct access to the hardware interface electronics 1140 and, by extension, the actuators 1120 and sensors 1130 of the exosuit 1100.

The applications 1114*a*, 1114*b*, 1114 are computer-readable programs that describe some function, functions, operating mode, or operating modes of the exosuit 1100. For example, application 1114*a* can describe a process for transmitting information about the wearer's posture to update a virtual avatar of the wearer that includes accessing information on a wearer's posture from the operating system 1112, maintaining communications with a remote system using the communications interface 1160, formatting the posture information, and sending the posture information to the remote system. The calibration service 1116 is a computer-readable program describing processes to store parameters describing properties of wearers, actuators 1120, and/or sensors 1130 of the exosuit 1100, to update those parameters based on operation of the actuators 1120, and/or sensors 1130 when a wearer is using the exosuit 1100, to make the parameters available to the operating system 1112 and/or applications 1114*a*, 1114*b*, 1114*c*, and other functions relating to the parameters. Note that applications 1114*a*, 1114*b*, 1114 and calibration service 1116 are intended as examples of computer-readable programs that can be run by the operating system 1112 of the controller 1110 to enable functions or operating modes of a exosuit 1100.

The operating system 1112 can provide for low-level control and maintenance of the hardware (e.g., 1120, 1130, 1140). In some examples, the operating system 1112 and/or hardware interface electronics 1540 can detect information about the exosuit 1100, the wearer, and/or the wearer's environment from one or more sensors 1130 at a constant specified rate. The operating system 1112 can generate an estimate of one or more states or properties of the exosuit 1100 or components thereof using the detected information. The operating system 1112 can update the generated estimate at the same rate as the constant specified rate or at a lower rate. The generated estimate can be generated from the detected information using a filter to remove noise, generate an estimate of an indirectly-detected property, or according to some other application. For example, the operating system 1112 can generate the estimate from the detected information using a Kalman filter to remove noise and to generate an estimate of a single directly or indirectly measured property of the exosuit 1100, the wearer, and/or the wearer's environment using more than one sensor. In some examples, the operating system can determine information about the wearer and/or exosuit 1100 based on detected information from multiple points in time. For example, the operating system 1100 can determine an eversion stretch and dorsiflexion stretch.

In some examples, the operating system 1112 and/or hardware interface electronics 1140 can operate and/or provide services related to operation of the actuators 1120. That is, in case where operation of the actuators 1120 requires the generation of control signals over a period of time, knowledge about a state or states of the actuators 1120, or other considerations, the operating system 1112 and/or hardware interface electronics 1140 can translate simple commands to operate the actuators 1120 (e.g., a command to generate a specified level of force using a twisted string actuator (TSA) of the actuators 1120) into the complex and/or state-based commands to the hardware interface electronics 1140 and/or actuators 1120 necessary to effect the simple command (e.g., a sequence of currents applied to windings of a motor of a TSA, based on a starting position of a rotor determined and stored by the operating system 1110, a relative position of the motor detected using an encoder, and a force generated by the TSA detected using a load cell).

In some examples, the operating system 1112 can further encapsulate the operation of the exosuit 1100 by translating a system-level simple command (e.g., a commanded level of force tension applied to the footplate) into commands for multiple actuators, according to the configuration of the exosuit 1100. This encapsulation can enable the creation of general-purpose applications that can effect a function of an exosuit (e.g., allowing a wearer of the exosuit to stretch his foot) without being configured to operate a specific model or type of exosuit (e.g., by being configured to generate a simple force production profile that the operating system 1112 and hardware interface electronics 1140 can translate into actuator commands sufficient to cause the actuators 1120 to apply the commanded force production profile to the footplate).

The operating system 1112 can act as a standard, multi-purpose platform to enable the use of a variety of exosuits having a variety of different hardware configurations to enable a variety of mechatronic, biomedical, human interface, training, rehabilitative, communications, and other applications. The operating system 1112 can make sensors 1130, actuators 1120, or other elements or functions of the exosuit 1100 available to remote systems in communication with the exosuit 1100 (e.g., using the communications interface 1160) and/or a variety of applications, daemons, services, or other computer-readable programs being executed by operating system 1112. The operating system 1112 can make the actuators, sensors, or other elements or functions available in a standard way (e.g., through an API, communications protocol, or other programmatic interface) such that applications, daemons, services, or other computer-readable programs can be created to be installed on, executed by, and operated to enable functions or operating modes of a variety of flexible exosuits having a variety of different configurations. The API, communications protocol, or other programmatic interface made available by the operating system 1112 can encapsulate, translate, or otherwise abstract the operation of the exosuit 1100 to enable the creation of such computer-readable programs that are able to operate to enable functions of a wide variety of differently-configured flexible exosuits.

Additionally or alternatively, the operating system 1112 can be configured to operate a modular flexible exosuit system (i.e., a flexible exosuit system wherein actuators, sensors, or other elements can be added or subtracted from a flexible exosuit to enable operating modes or functions of the flexible exosuit). In some examples, the operating system 1112 can determine the hardware configuration of the exosuit 1100 dynamically and can adjust the operation of the exosuit 1100 relative to the determined current hardware configuration of the exosuit 1100. This operation can be performed in a way that was 'invisible' to computer-readable programs (e.g., 1114*a*, 1114*b*, 1114*c*) accessing the functionality of the exosuit 1100 through a standardized programmatic interface presented by the operating system 1112. For example, the computer-readable program can indicate to the operating system 1112, through the standardized programmatic interface, that a specified level of torque was to be applied to an ankle of a wearer of the exosuit 1100. The operating system 1112 can responsively determine a pattern of operation of the actuators 1120, based on the determined hardware configuration of the exosuit 1100, sufficient to apply the specified level of torque to the ankle of the wearer.

In some examples, the operating system 1112 and/or hardware interface electronics 1140 can operate the actuators 1120 to ensure that the exosuit 1100 does not operate to directly cause the wearer to be injured and/or elements of the exosuit 1100 to be damaged. In some examples, this can include not operating the actuators 1120 to apply forces and/or torques to the body of the wearer that exceeded some maximum threshold. This can be implemented as a watchdog process or some other computer-readable program that can be configured (when executed by the controller 1110) to monitor the forces being applied by the actuators 1120 (e.g., by monitoring commands sent to the actuators 1120 and/or monitoring measurements of forces or other properties detected using the sensors 1130) and to disable and/or change the operation of the actuators 1120 to prevent injury of the wearer. Additionally or alternatively, the hardware interface electronics 1140 can be configured to include circuitry to prevent excessive forces and/or torques from being applied to the wearer (e.g., by channeling to a comparator the output of a load cell that is configured to measure the force generated by a TSA, and configuring the comparator to cut the power to the motor of the TSA when the force exceeded a specified level).

In some examples, operating the actuators 1120 to ensure that the exosuit 1100 does not damage itself can include a watchdog process or circuitry configured to prevent over-current, over-load, over-rotation, or other conditions from occurring that can result in damage to elements of the exosuit 1100. For example, the hardware interface electronics 1140 can include a metal oxide varistor, breaker, shunt diode, or other element configured to limit the voltage and/or current applied to a winding of a motor.

Note that the above functions described as being enabled by the operating system 1112 can additionally or alternatively be implemented by applications 1114a, 1114b, 1114c, services, drivers, daemons, or other computer-readable programs executed by the controller 1100. The applications, drivers, services, daemons, or other computer-readable programs can have special security privileges or other properties to facilitate their use to enable the above functions.

The operating system 1112 can encapsulate the functions of the hardware interface electronics 1140, actuators 1120, and sensors 1130 for use by other computer-readable programs (e.g., applications 1114a, 1114b, 1114c, calibration service 1116), by the user (through the user interface 1150), and/or by some other system (i.e., a system configured to communicate with the controller 1110 through the communications interface 1960). The encapsulation of functions of the exosuit 1100 can take the form of application programming interfaces (APIs), i.e., sets of function calls and procedures that an application running on the controller 1110 can use to access the functionality of elements of the exosuit 1100. In some examples, the operating system 1112 can make available a standard 'exosuit API' to applications being executed by the controller 1110. The 'exosuit API' can enable applications 1114a, 1114b, 1114c to access functions of the exosuit 1100 without requiring those applications 1114a, 1114b, 1114c to be configured to generate whatever complex, time-dependent signals are necessary to operate elements of the exosuit 1100 (e.g., actuators 1120, sensors 1130).

The 'exosuit API' can allow applications 1114a, 1114b, 1114c to send simple commands to the operating system 1112 (e.g., 'begin storing mechanical energy from the ankle of the wearer when the foot of the wearer contacts the ground') in such that the operating system 1112 can interpret those commands and generate the command signals to the hardware interface electronics 1140 or other elements of the exosuit 1100 that are sufficient to effect the simple commands generated by the applications 1114a, 1114b, 1114c (e.g., determining whether the foot of the wearer has contacted the ground based on information detected by the sensors 1130, responsively applying high voltage to an exotendon that crosses the user's ankle).

The 'exosuit API' can be an industry standard (e.g., an ISO standard), a proprietary standard, an open-source standard, or otherwise made available to individuals that can then produce applications for exosuits. The 'exosuit API' can allow applications, drivers, services, daemons, or other computer-readable programs to be created that are able to operate a variety of different types and configurations of exosuits by being configured to interface with the standard 'exosuit API' that is implemented by the variety of different types and configurations of exosuits. Additionally or alternatively, the 'exosuit API' can provide a standard encapsulation of individual exosuit-specific actuators (i.e., actuators that apply forces to specific body segments, where differently-configured exosuits may not include an actuator that applies forces to the same specific body segments) and can provide a standard interface for accessing information on the configuration of whatever exosuit is providing the 'exosuit API'. An application or other program that accesses the 'exosuit API' can access data about the configuration of the exosuit (e.g., locations and forces between body segments generated by actuators, specifications of actuators, locations and specifications of sensors) and can generate simple commands for individual actuators (e.g., generate a force of 30 newtons for 50 milliseconds) based on a model of the exosuit generated by the application and based on the information on the accessed data about the configuration of the exosuit. Additional or alternate functionality can be encapsulated by an 'exosuit API' according to an application.

Applications 1114a, 1114b, 1114c can individually enable all or parts of the functions and operating modes of a flexible exosuit described herein. For example, an application can enable haptic control of a robotic system by transmitting postures, forces, torques, and other information about the activity of a wearer of the exosuit 1100 and by translating received forces and torques from the robotic system into haptic feedback applied to the wearer (i.e., forces and torques applied to the body of the wearer by actuators 1120 and/or haptic feedback elements). In another example, an application can enable a wearer to locomote more efficiently by submitting commands to and receiving data from the operating system 1112 (e.g., through an API) such that actuators 1120 of the exosuit 1100 assist the movement of the user, extract negative work from phases of the wearer's locomotion and inject the stored work to other phases of the wearer's locomotion, or other methods of operating the exosuit 1100. Applications can be installed on the controller 1110 and/or on a computer-readable storage medium included in the exosuit 1100 by a variety of methods. Applications can be installed from a removable computer-readable storage medium or from a system in communication with the controller 1110 through the communications interface 1960. In some examples, the applications can be installed from a web site, a repository of compiled or un-compiled programs on the Internet, an online store (e.g., Google Play, iTunes App Store), or some other source. Further, functions of the applications can be contingent upon the controller 1110 being in continuous or periodic communication with a remote system (e.g., to receive updates, authenticate the application, to provide information about current environmental conditions).

The exosuit 1100 illustrated in FIG. 11 is intended as an illustrative example. Other configurations of flexible exosuits and of operating systems, kernels, applications, drivers, services, daemons, or other computer-readable programs are anticipated. For example, an operating system configured to operate an exosuit can include a real-time operating system component configured to generate low-level commands to operate elements of the exosuit and a non-real-time component to enable less time-sensitive functions, like a clock on a user interface, updating computer-readable programs stored in the exosuit, or other functions. A exosuit can include more than one controller; further, some of those controllers can be configured to execute real-time applications, operating systems, drivers, or other computer-readable programs (e.g., those controllers were configured to have very short interrupt servicing routines, very fast thread switching, or other properties and functions relating to latency-sensitive computations) while other controllers are configured to enable less time-sensitive functions of a flexible exosuit. Additional configurations and operating modes of an exosuit are anticipated. Further, control systems configured as described herein can additionally or alternatively be configured to enable the operation of devices and systems other than exosuit; for example, control systems as described herein can be configured to operate robots, rigid exosuits or exoskeletons, assistive devices, prosthetics, or other mechatronic devices.

Control of actuators of an exosuit can be implemented in a variety of ways according to a variety of control schemes. Generally, one or more hardware and/or software controllers can receive information about the state of the flexible exosuit, a wearer of the exosuit, and/or the environment of the exosuit from sensors disposed on or within the exosuit and/or a remote system in communication with the exosuit. The one or more hardware and/or software controllers can then generate a control output that can be executed by actuators of the exosuit to affect a commanded state of the exosuit and/or to enable some other application. One or more software controllers can be implemented as part of an operating system, kernel, driver, application, service, daemon, or other computer-readable program executed by a processor included in the exosuit.

In some embodiments, a powered assistive exosuit intended primarily for assistive functions can also be adapted to perform exosuit functions. In one embodiment, an assistive exosuit similar to the embodiments described in US Publication No. 2018/0056104, that is used for assistive functions may be adapted to perform exosuit functions. Embodiments of such an assistive exosuit typically include FLAs approximating muscle groups such as hip flexors, gluteal/hip extensors, spinal extensors, or abdominal muscles. In the assistive modes of these exosuits, these FLAs provide assistance for activities such as moving between standing and seated positions, walking, and postural stability. Actuation of specific FLAs within such an exosuit system may also provide stretching assistance. Typically, activation of one or more FLAs approximating a muscle group can stretch the antagonist muscles. For example, activation of one or more FLAs approximating the abdominal muscles might stretch the spinal extensors, or activation of one or more FLAs approximating gluteal/hip extensor muscles can stretch the hip flexors. The exosuit may be adapted to detect when the wearer is ready to initiate a stretch and perform an automated stretching regimen; or the wearer may indicate to the suit to initiate a stretching regimen.

It can be appreciated that assistive exosuits may have multiple applications. Assistive exosuits may be prescribed for medical applications. These may include therapeutic applications, such as assistance with exercise or stretching regimens for rehabilitation, disease mitigation or other therapeutic purposes. Mobility-assistance devices such as wheelchairs, walkers, crutches and scooters are often prescribed for individuals with mobility impairments. Likewise, an assistive exosuit may be prescribed for mobility assistance for patients with mobility impairments. Compared with mobility assistance devices such as wheelchairs, walkers, crutches and scooters, an assistive exosuit may be less bulky, more visually appealing, and conform with activities of daily living such as riding in vehicles, attending community or social functions, using the toilet, and common household activities.

An assistive exosuit may additionally function as primary apparel, fashion items or accessories. The exosuit may be stylized for desired visual appearance. The stylized design may reinforce visual perception of the assistance that the exosuit is intended to provide. For example, an assistive exosuit intended to assist with torso and upper body activities may present a visual appearance of a muscular torso and upper body. Alternatively, the stylized design may be intended to mask or camouflage the functionality of the assistive exosuit through design of the base layer, electro/mechanical integration or other design factors.

Similarly to assistive exosuits intended for medically prescribed mobility assistance, assistive exosuits may be developed and utilized for non-medical mobility assistance, performance enhancement and support. For many, independent aging is associated with greater quality of life, however activities may become more limited with time due to normal aging processes. An assistive exosuit may enable aging individuals living independently to electively enhance their abilities and activities. For example, gait or walking assistance could enable individuals to maintain routines such as social walking or golf. Postural assistance may render social situations more comfortable, with less fatigue. Assistance with transitioning between seated and standing positions may reduce fatigue, increase confidence, and reduce the risk of falls. These types of assistance, while not explicitly medical in nature, may enable more fulfilling, independent living during aging processes.

Athletic applications for an assistive exosuit are also envisioned. In one example, an exosuit may be optimized to assist with a particular activity, such as cycling. In the cycling example, FLAs approximating gluteal or hip extensor muscles may be integrated into bicycle clothing, providing assistance with pedaling. The assistance could be varied based on terrain, fatigue level or strength of the wearer, or other factors. The assistance provided may enable increased performance, injury avoidance, or maintenance of performance in the case of injury or aging. It can be appreciated that assistive exosuits could be optimized to assist with the demands of other sports such as running, jumping, swimming, skiing, or other activities. An athletic assistive exosuit may also be optimized for training in a particular sport or activity. Assistive exosuits may guide the wearer in proper form or technique, such as a golf swing, running stride, skiing form, swimming stroke, or other components of sports or activities. Assistive exosuits may also provide resistance for strength or endurance training. The provided resistance may be according to a regimen, such as high intensity intervals.

Assistive exosuit systems as described above may also be used in gaming applications. Motions of the wearer, detected by the suit, may be incorporated as a game controller system. For example, the suit may sense wearer's motions that simulate running, jumping, throwing, dancing, fighting, or other motions appropriate to a particular game. The suit may provide haptic feedback to the wearer, including resistance or assistance with the motions performed or other haptic feedback to the wearer.

Assistive exosuits as described above may be used for military or first responder applications. Military and first responder personnel are often to be required to perform arduous work where safety or even life may be at stake. An assistive exosuit may provide additional strength or endurance as required for these occupations. An assistive exosuit may connect to one or more communication networks to provide communication services for the wearer, as well as remote monitoring of the suit or wearer.

Assistive exosuits as described above may be used for industrial or occupational safety applications. Exosuits may provide more strength or endurance for specific physical tasks such as lifting or carrying or repetitive tasks such as assembly line work. By providing physical assistance, assistive exosuits may also help avoid or prevent occupational injury due overexertion or repetitive stress.

Assistive exosuits as described above may also be configured as home accessories. Home accessory assistive exosuits may assist with household tasks such as cleaning or yard work, or may be used for recreational or exercise purposes. The communication capabilities of an assistive exosuit may connect to a home network for communication, entertainment or safety monitoring purposes.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art can appreciate that the conception, upon which this disclosure is based, may readily be utilized as a basis for the designing of other structures, systems, methods and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. An exosuit system, comprising:
    an exosuit comprising a base layer, a power layer, and a plurality of sensors, wherein the exosuit is operative to provide the plurality of assistive movements; and
    control circuitry coupled to the power layer and the plurality of sensors, the control circuitry operative to:
        receive data from the plurality of sensors during an exosuit use period;
        identify segments of relatively high user activity and segments of relatively low user activity within the received data that occurred during the exosuit use period, wherein the segments of relatively low user activity occur in between the segments of relatively high user activity;
        analyze data associated with the segments of relatively low user activity to obtain a plurality of posture sessions performed by a user of the exosuit during the exosuit use period, wherein each of the plurality of posture sessions specifies a posture position comprising a forward/backward lean angle and a left/right lean angle;
        monitor changes in the posture position for each of the plurality of posture sessions over a fixed time duration to identify a user posture pattern;
        selectively provide informational feedback via the exosuit based on the plurality of posture sessions; and
        engage pre-emptive corrective assistance based on the user posture pattern.

2. The exosuit system of claim 1, wherein the control circuitry is operative to:
    cluster each of the plurality of posture sessions according to one of a plurality of clusters, wherein each of the plurality clusters correspond to a time frame within the exosuit use period; and
    classify each of the plurality of clusters according to a representative posture position indicative of posture positions associated with a particular cluster.

3. The exosuit system of claim 2, wherein the control circuitry is operative to:
    observe changes in the representative posture positions throughout the exosuit use period; adjust the feedback provided based on the observed changes in the representative posture positions.

4. The exosuit system of claim 1, wherein the control circuitry is operative to aggregate the plurality of posture sessions over multiple exosuit use periods.

5. The exosuit system of claim 4, wherein the control circuitry is operative to:
    analyze the aggregated posture sessions; and
    provide feedback based on the analyzed aggregated posture sessions.

6. The exosuit system of claim 1, wherein the control circuitry is operative to discard data associated with the segments of relatively high user activity.

7. The exosuit system of claim 6, wherein the control circuitry is operative to compress the data associated with each posture session.

8. The exosuit system of claim 1, wherein the exosuit use period comprises a fixed number of hours within a day, a period of several days, a week, a month, or a year.

9. The exosuit system of claim 1, wherein the informational feedback comprises a haptic cue, an auditory cue, or a visual cue.

10. A method for using an exosuit comprising a base layer, a power layer, and a plurality of sensors, the method comprising:
    receiving data from the plurality of sensors during an exosuit use period;
    identifying segments of relatively high user activity and segments of relatively low user activity within the received data that occurred during the exosuit use period, wherein the segments of relatively low user activity occur in between the segments of relatively high user activity and wherein segments of relatively low user activity correspond to user standing events and user sitting events;
    storing data associated with the segments of relatively low user activity;
    discarding data associated with the segments of relatively high user activity;
    analyzing stored data associated with the segments of relatively low user activity to obtain a plurality of posture sessions performed by a user of the exosuit during the exosuit use period, wherein each of the plurality of posture sessions comprises a posture position and a posture duration, wherein the posture position is classified into one of a plurality of different left/right tilt angle ranges and into one of a plurality of different forward/backward tilt angle ranges;

monitoring changes in the posture position for each of the plurality of posture sessions over a fixed time duration to identify a user posture pattern;

selectively providing feedback via the exosuit based on a combination of which left/right tilt angle range and which forward/backward tilt angle range the posture position is in and the posture duration of each of the plurality of posture sessions; and engaging pre-emptive corrective assistance based on the user posture pattern.

11. The method of claim 10, wherein when the posture position for one of the posture sessions is classified as a relatively poor posture position and the posture duration exceeds a first time threshold, providing the feedback via the exosuit.

12. The method of claim 11, wherein the feedback comprises exosuit assistance motion, an audio cue, or a haptic cue.

13. The method of claim 10, wherein when the posture position for one of the posture sessions is classified as a relatively poor posture position and the posture duration is less than a second time threshold, preventing the feedback.

14. The method of claim 10, wherein the posture position comprises a forward/backward lean angle and a left/right lean angle.

15. The method of claim 10, further comprising clustering the plurality of posture sessions according to the posture position.

16. The method of claim 10, further comprising clustering the plurality of posture sessions according to the posture position and a time of day.

17. The method of claim 10, further comprising:
discarding data associated with the segments of relatively high user activity; and
compressing the data associated with each posture session.

18. The method of claim 17, further comprising:
uploading the compressed data to a server via a wireless or wired connection.

19. The method of claim 10, further comprising verifying that the feedback is improving posture.

20. The method of claim 10, further comprising:
detecting an improper fit of a portion of the exosuit based on the plurality of posture sessions; and
providing notice to the user of the exosuit of the improper fit.

* * * * *